(12) United States Patent
Copp et al.

(10) Patent No.: US 9,737,339 B2
(45) Date of Patent: Aug. 22, 2017

(54) POSTERIO SPINAL FIXATION

(75) Inventors: Matthew Copp, San Diego, CA (US); Christopher M. Campbell, Temecula, CA (US); G. Bryan Cornwall, San Diego, CA (US); Eric Dasso, San Diego, CA (US); Frank M. Phillips, Highland Park, IL (US)

(73) Assignee: NuVasive, Inc., San Diego, CA (US)

( * ) Notice: Subject to any disclaimer, the term of this patent is extended or adjusted under 35 U.S.C. 154(b) by 2142 days.

(21) Appl. No.: 11/667,365

(22) PCT Filed: Sep. 8, 2005

(86) PCT No.: PCT/US2005/032300
§ 371 (c)(1),
(2), (4) Date: May 8, 2007

(87) PCT Pub. No.: WO2006/029373
PCT Pub. Date: Mar. 16, 2006

(65) Prior Publication Data
US 2008/0183214 A1    Jul. 31, 2008

Related U.S. Application Data

(60) Provisional application No. 60/608,476, filed on Sep. 8, 2004.

(51) Int. Cl.
*A61B 17/70*    (2006.01)
*A61B 17/02*    (2006.01)

(52) U.S. Cl.
CPC ...... *A61B 17/7037* (2013.01); *A61B 17/7005* (2013.01); *A61B 17/708* (2013.01); *A61B 17/7085* (2013.01); *A61B 17/7092* (2013.01); *A61B 17/7004* (2013.01); *A61B 17/7011* (2013.01); *A61B 17/7032* (2013.01); *A61B 17/7076* (2013.01); *A61B 17/7091* (2013.01); *A61B 2017/0256* (2013.01)

(58) Field of Classification Search
CPC . A61B 17/70; A61B 17/7005; A61B 17/7032; A61B 17/7085; A61B 17/708; A61B 17/7083; A61F 2250/0062; A61F 2/4611; A61F 2002/30607
USPC .................................. 606/246, 250, 260, 264
See application file for complete search history.

(56) References Cited

U.S. PATENT DOCUMENTS

| | | | |
|---|---|---|---|
| 3,848,601 A | * | 11/1974 | Ma .................... A61B 17/1604 606/86 A |
| 4,655,216 A | | 4/1987 | Tischer |
| 5,540,688 A | * | 7/1996 | Navas .......................... 606/266 |
| 5,720,751 A | | 2/1998 | Jackson |

(Continued)

FOREIGN PATENT DOCUMENTS

| | | |
|---|---|---|
| DE | 4238339 | 5/1994 |
| EP | 1470790 | 10/2004 |

(Continued)

*Primary Examiner* — Brian Pellegrino
(74) *Attorney, Agent, or Firm* — Bradley Arant Boult Cummings; Rory Schermerhorn

(57) ABSTRACT

This application describes a spinal fixation system. The spinal fixation system includes at least a rod member having shaped ends, at least two pedicle screws capable of receiving the shaped ends of the rod member, and a system for introducing the rod member and pedicle screws in a minimally invasive fashion.

36 Claims, 40 Drawing Sheets

(56) References Cited

U.S. PATENT DOCUMENTS

| | | | |
|---|---|---|---|
| 5,984,923 A * | 11/1999 | Breard | 606/260 |
| 6,113,639 A * | 9/2000 | Ray | A61F 2/4684 623/17.16 |
| 6,139,549 A | 10/2000 | Keller | |
| 6,183,472 B1 | 2/2001 | Lutz | |
| 6,235,028 B1 | 5/2001 | Brumfield et al. | |
| 6,299,616 B1 | 10/2001 | Beger | |
| 6,379,364 B1 | 4/2002 | Brace et al. | |
| 6,440,133 B1 | 8/2002 | Beale et al. | |
| 6,511,484 B2 | 1/2003 | Torode et al. | |
| 6,530,929 B1 | 3/2003 | Justis et al. | |
| 6,547,795 B2 | 4/2003 | Schneiderman | |
| 6,648,888 B1 | 11/2003 | Shluzas | |
| 6,929,606 B2 | 8/2005 | Ritland | |
| 6,951,538 B2 | 10/2005 | Ritland | |
| 7,008,422 B2 | 3/2006 | Foley et al. | |
| 7,011,660 B2 | 3/2006 | Sherman | |
| 7,179,261 B2 | 2/2007 | Sicvol et al. | |
| 7,188,626 B2 | 3/2007 | Foley et al. | |
| 7,481,813 B1 | 1/2009 | Purcell | |
| 2001/0021853 A1 | 9/2001 | Heckele et al. | |
| 2002/0161368 A1* | 10/2002 | Foley et al. | 606/61 |
| 2003/0199872 A1 | 10/2003 | Markworth et al. | |
| 2003/0208203 A1 | 11/2003 | Lim et al. | |
| 2004/0138662 A1 | 7/2004 | Landry et al. | |
| 2004/0143265 A1 | 7/2004 | Landry et al. | |
| 2004/0147937 A1 | 7/2004 | Dunbar, Jr. et al. | |
| 2004/0172022 A1 | 9/2004 | Landry et al. | |
| 2005/0021031 A1 | 1/2005 | Foley et al. | |
| 2005/0065517 A1 | 3/2005 | Chin | |
| 2005/0085813 A1 | 4/2005 | Spitler et al. | |
| 2005/0131408 A1 | 6/2005 | Sicvol et al. | |
| 2005/0131419 A1 | 6/2005 | McCord et al. | |
| 2005/0131420 A1 | 6/2005 | Techiera et al. | |
| 2005/0131421 A1 | 6/2005 | Anderson et al. | |
| 2005/0131422 A1 | 6/2005 | Anderson et al. | |
| 2005/0154389 A1 | 7/2005 | Selover et al. | |
| 2005/0192570 A1 | 9/2005 | Jackson et al. | |
| 2005/0192579 A1 | 9/2005 | Jackson | |
| 2005/0192589 A1 | 9/2005 | Raymond et al. | |
| 2005/0215999 A1 | 9/2005 | Birkmeyer et al. | |
| 2005/0228380 A1 | 10/2005 | Moore et al. | |
| 2005/0228400 A1 | 10/2005 | Chao et al. | |
| 2005/0245928 A1 | 11/2005 | Colleran et al. | |
| 2006/0036244 A1 | 2/2006 | Spitler et al. | |
| 2006/0036255 A1 | 2/2006 | Pond, Jr. et al. | |
| 2006/0069391 A1 | 3/2006 | Jackson | |
| 2006/0074418 A1 | 4/2006 | Jackson | |
| 2006/0079894 A1 | 4/2006 | Colleran et al. | |
| 2006/0079909 A1 | 4/2006 | Runco | |
| 2006/0084993 A1 | 4/2006 | Landry et al. | |
| 2006/0089651 A1 | 4/2006 | Trudeau et al. | |
| 2006/0095035 A1 | 5/2006 | Jones et al. | |
| 2006/0106380 A1 | 5/2006 | Colleran et al. | |
| 2006/0106394 A1 | 5/2006 | Colleran et al. | |
| 2006/0111712 A1 | 5/2006 | Jackson | |
| 2006/0111715 A1 | 5/2006 | Jackson | |
| 2006/0122597 A1 | 6/2006 | Jones et al. | |
| 2006/0142761 A1 | 6/2006 | Landry et al. | |
| 2006/0200132 A1 | 9/2006 | Chao et al. | |
| 2006/0247658 A1 | 11/2006 | Pond, Jr. et al. | |
| 2006/0264934 A1 | 11/2006 | Fallin | |
| 2006/0281838 A1 | 12/2006 | Steinhausler et al. | |
| 2006/0293693 A1 | 12/2006 | Farr et al. | |
| 2007/0049931 A1 | 3/2007 | Justis et al. | |
| 2007/0167949 A1 | 7/2007 | Altarac et al. | |
| 2007/0167954 A1 | 7/2007 | Sicvol et al. | |
| 2008/0073323 A1 | 3/2008 | Full et al. | |
| 2008/0091213 A1 | 4/2008 | Jackson | |
| 2008/0288005 A1 | 11/2008 | Jackson | |
| 2010/0004696 A1 | 1/2010 | Jackson | |

FOREIGN PATENT DOCUMENTS

| | | |
|---|---|---|
| EP | 1574175 | 9/2005 |
| WO | 0128436 | 4/2001 |
| WO | 2004041100 | 5/2004 |
| WO | 2005058141 | 6/2005 |
| WO | 2006042188 | 4/2006 |
| WO | 2006057837 | 6/2006 |
| WO | 2006091863 | 8/2006 |
| WO | 2006127425 | 11/2006 |
| WO | 2007021588 | 2/2007 |
| WO | 2008051255 | 5/2008 |

* cited by examiner

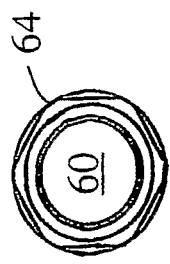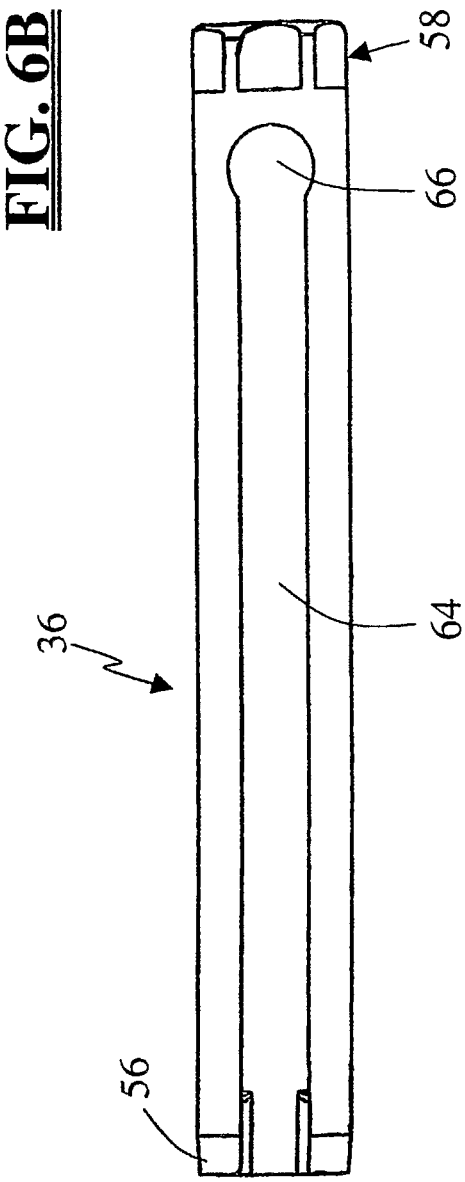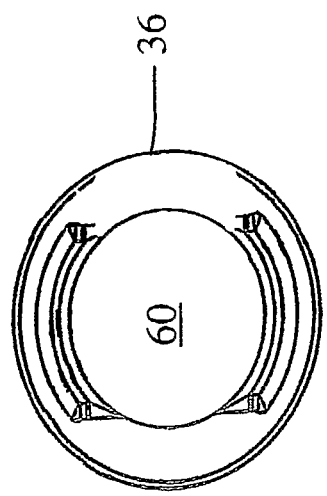

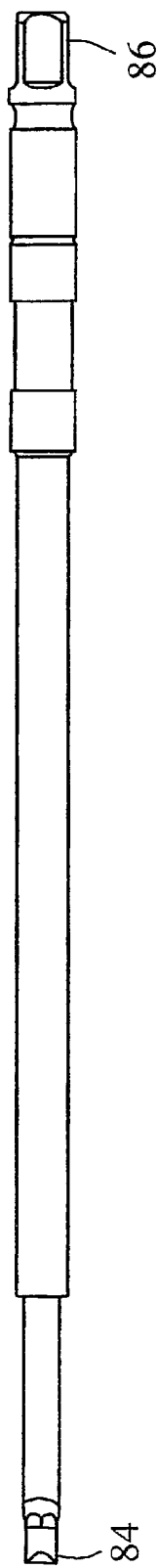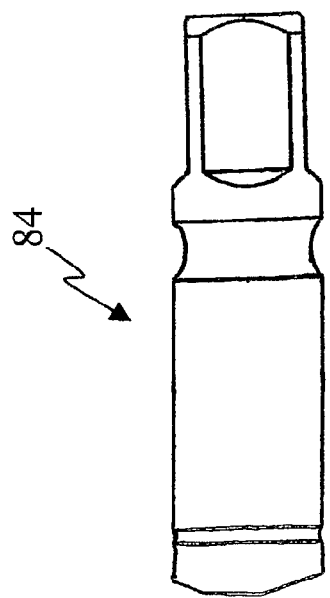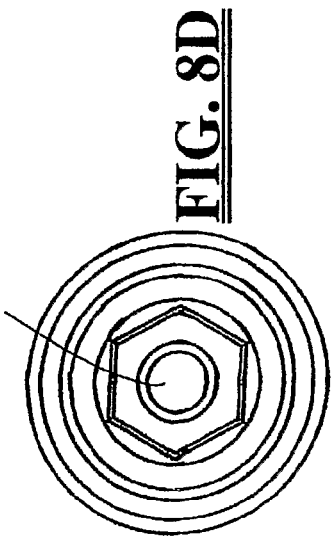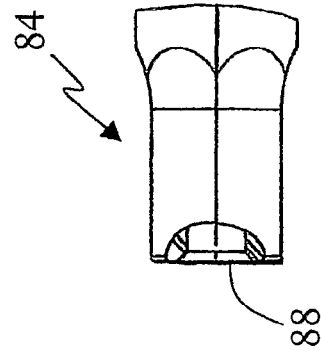
FIG. 8A
FIG. 8B
FIG. 8C
FIG. 8D
FIG. 8E

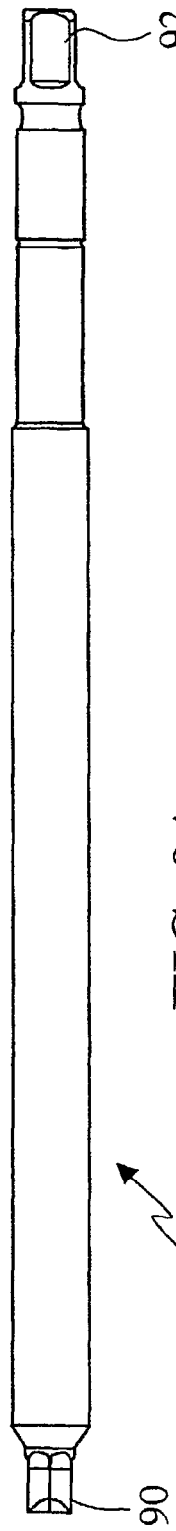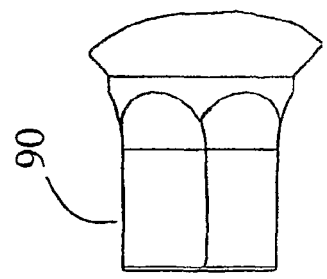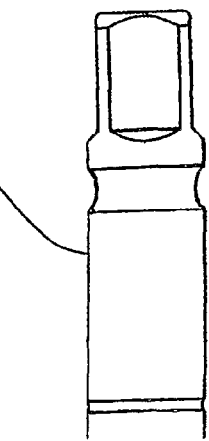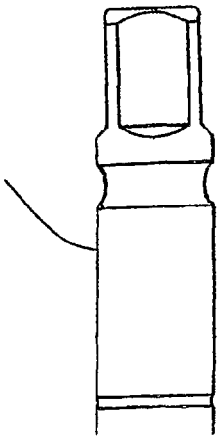

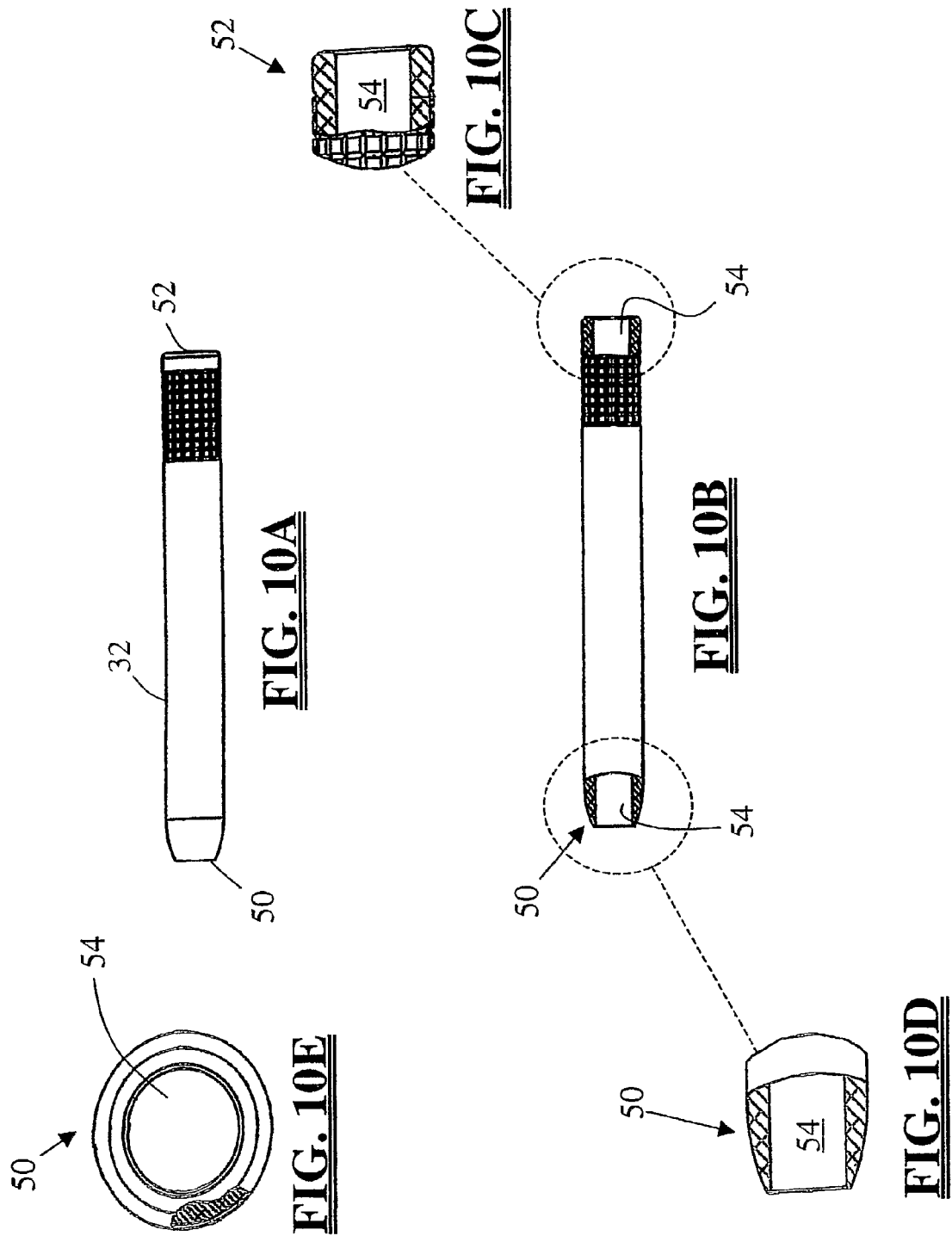

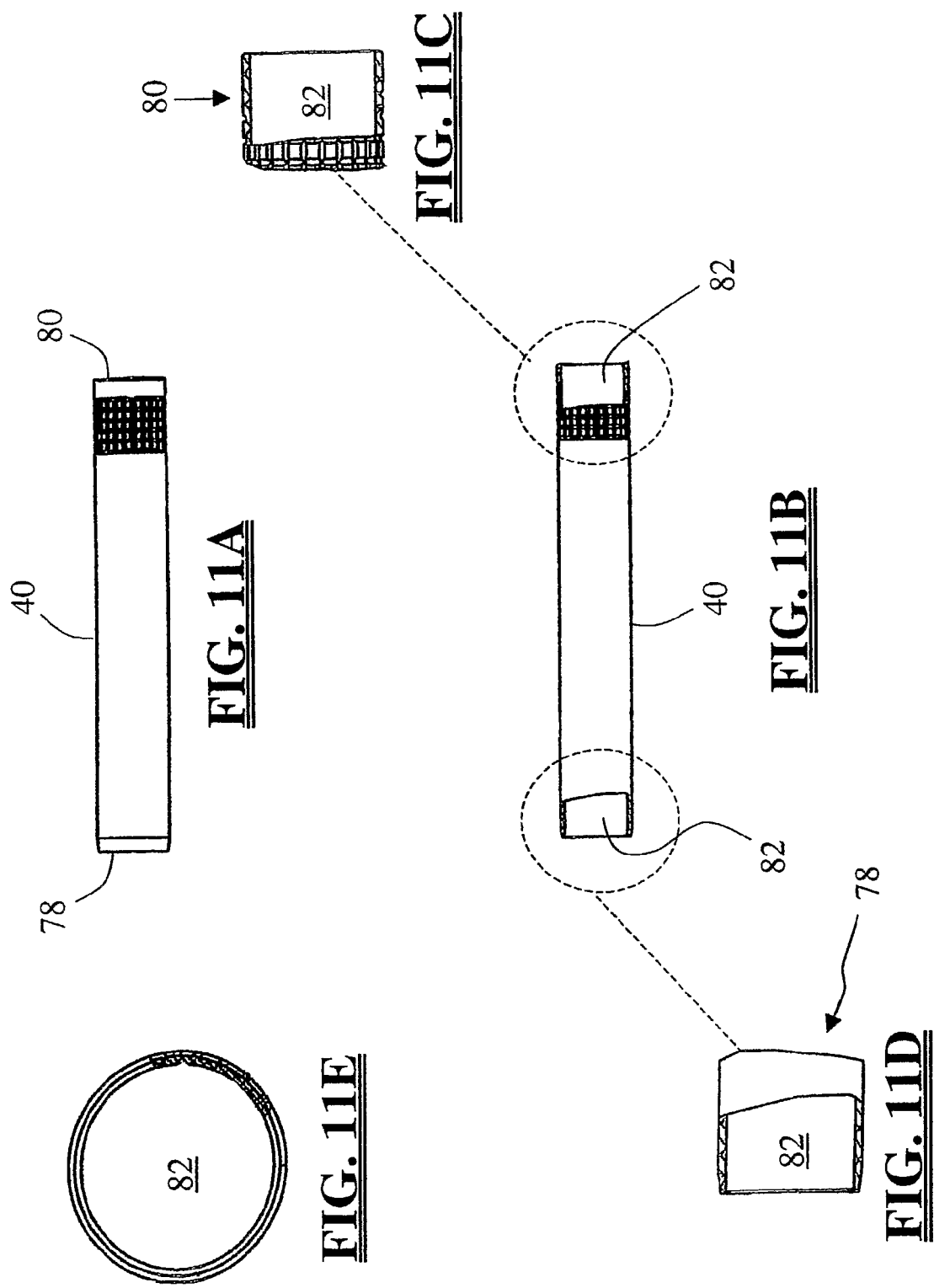

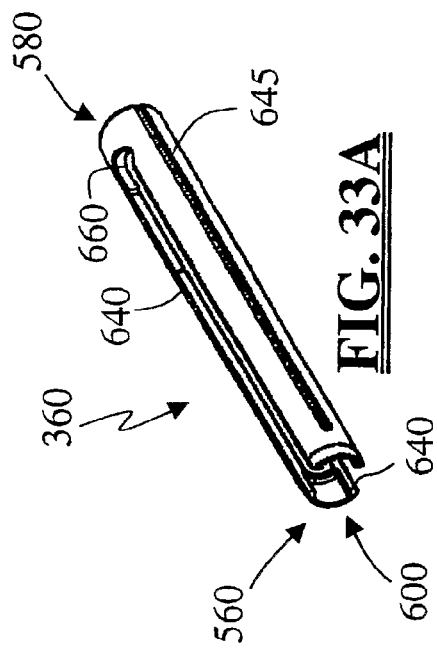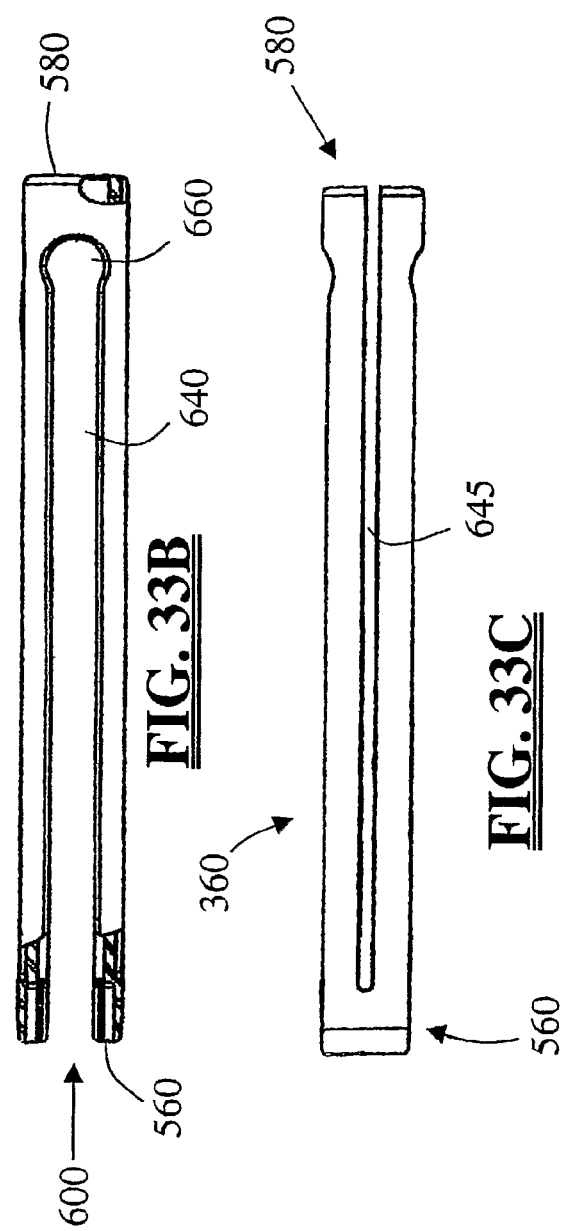

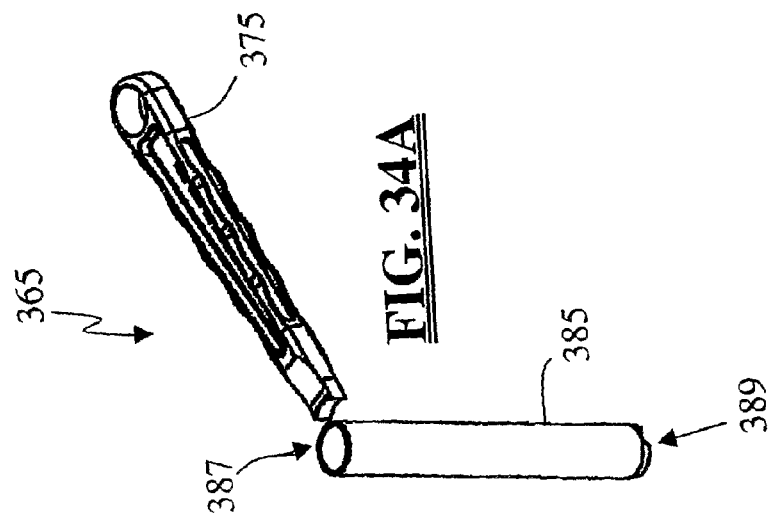
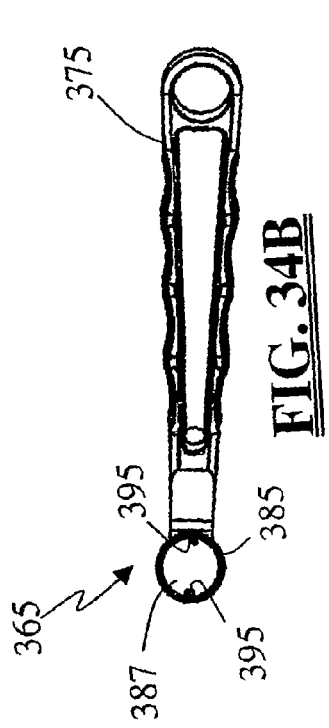
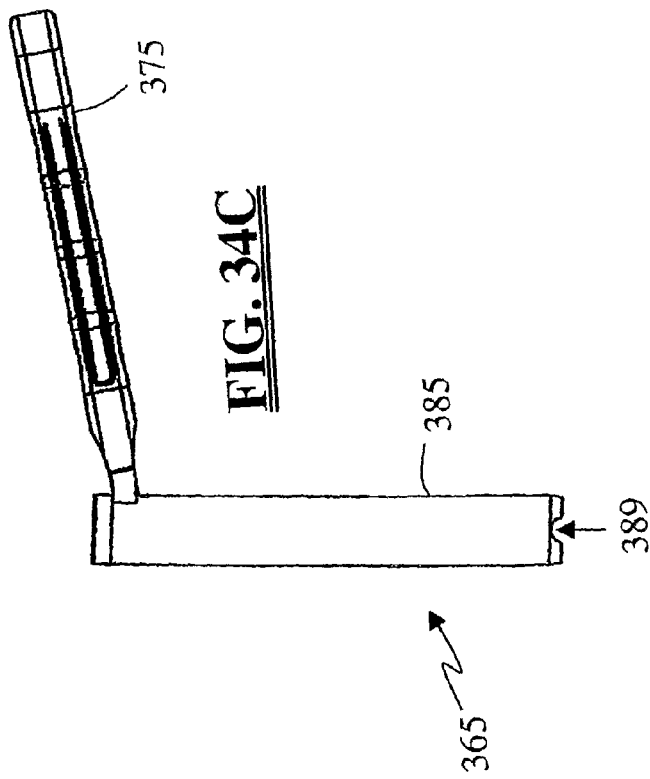

POSTERIO SPINAL FIXATION

CROSS REFERENCE TO RELATED APPLICATIONS

This is an International Patent Application claiming the benefit of priority under 35 USC 119(e) of commonly owned and U.S. Provisional Patent Application No. 60/608,476 entitled "System and Method for Performing Spinal Fixation," filed Sep. 8, 2004, the entire contents of which is hereby expressly incorporated by reference into this disclosure as if set forth fully herein.

BACKGROUND OF THE INVENTION

I. Field of the Invention

The present invention relates to medical devices and methods generally aimed at spinal surgery. In particular, the disclosed system and associated methods relate to performing spinal fixation.

II. Discussion of the Prior Art

Fixation systems are often surgically implanted into a patient to aid in the stabilization of a damaged spine or to aid in the correction of other spinal geometric deformities. Spinal fixation systems are often constructed as a framework stabilizing a particular section of the spine. Existing systems often use a combination of rods, plates, pedicle screws and bone hooks for fixing the framework to the affected vertebrae. The configuration required for each patient varies due to the patient's specific anatomical characteristics and ailments. As a result, there is a need for a modular spinal fixation system that allows for a large degree of custom configurations. Existing system are limited in their ability to be used for percutaneous procedures and, of those available, various drawbacks exist.

The present invention is directed at addressing this need and eliminating, or at least reducing, the effects of the shortcomings of the prior art.

SUMMARY OF THE INVENTION

The spinal fixation system of the present invention is designed to effect fixation between at least two vertebral bodies within a spine and, in an important aspect, is configured to be introduced into the spine in a tissue sparing, minimally disruptive manner. The spinal fixation system of the present invention includes both a "single level" embodiment for effecting fixation between two adjacent vertebral bodies within a spine and a "multi-level" embodiment for effecting fixation between more than two vertebral bodies within the spine. In the single level embodiment, the spinal fixation system includes at least one pair of pedicle screws (one for each adjacent vertebral body) and an elongated connecting member for connecting the two pedicle screws. In the "multi-level" embodiment, the spinal fixation system includes an elongated connecting member that spans at least three vertebrae (e.g. two vertebral levels) and may include a corresponding number of pedicle screws as the number of vertebrae to be affixed or at least two pedicle screws securing the superior and inferior vertebral bodies (with no pedicle screw coupled at one or more of the centrally located vertebral bodies). The pedicle screws in either embodiment may have a shaft rigidly fixed to a housing (so-called "fixed-axis" screws) and/or have a shaft adjustably coupled to a housing (so-called "poly-axial" or "multi-axial" screws). The pedicle screws may be applied between the vertebral bodies on one side of the spine or bilaterally on both sides of the spine.

In an important aspect, the elongated connecting members are equipped with shaped ends dimensioned to be received within correspondingly shaped receiving areas within the pedicle screw housing. As will be described in detail herein, the shaped ends of the connecting members are advantageous in terms of facilitating the ease of introduction into, and engagement within, the pedicle screw housing. The shaped ends of the connecting members are also advantageous when employed with multi-axial pedicle screws by allowing a surgeon to perform "instrument free" compression and/or distraction of the vertebral bodies by rotating the pedicle screw housing about the shaped end of the connecting member. This is accomplished via the use of a minimally disruptive introduction system forming part of the present invention.

The minimally disruptive introduction system of the present invention includes a guide assembly for guiding (as a first step) each pedicle screw into the respective vertebra and (as a second step) guiding the connecting element such that the shaped ends are disposed within the correspondingly shaped receiving area of the pedicle screw housings. The minimally disruptive introduction system may also include a variety of additional instruments for facilitating the introduction of the pedicle screws (e.g., a spinal access needle (e.g. Jamshidi needle), a guide wire (e.g. K-wire), a pedicle screw driver, a cannulated tap, etc. . . . ), instruments for locking the connecting member to the pedicle screws (e.g., a locking element driver, etc. . . . ), and instruments for insulating the various components of the spinal fixation system and/or introduction system during optional EMG-based pedicle integrity testing during pilot hole formation, preparation, and screw introduction. The minimally disruptive introduction system is advantageous in that it provides the ability to access the spinal target site with a generally small incision and with minimal tissue disruption.

BRIEF DESCRIPTION OF THE DRAWINGS

Other objects and advantages of the invention will become apparent upon reading the following detailed description and upon reference to the drawings in which:

FIGS. 6A-6C illustrate in detail various aspects of the guide member forming part of the guide assembly according to one exemplary embodiment of the present invention;

FIG. 8A-8E illustrate in detail various aspects of the pedicle screw driver according to an exemplary embodiment of the present invention;

FIGS. 9A-9E illustrate in detail various aspects of the lock screw driver 44 according to an exemplary embodiment of the present invention;

FIGS. 10A-10E illustrate in detail various aspects of the tap insulator 32 according to one exemplary embodiment of the present invention;

FIGS. 11A-11E illustrate in detail various aspects of the guide insulator 40 according to an exemplary embodiment of the present invention;

FIGS. 26-7 illustrate a method of performing compression by deflecting guide members away from each other during the minimally invasive insertion of the spinal fixation system of FIG. 1, according to an exemplary embodiment of the present invention;

FIGS. 33A-33C illustrate in detail various aspects of the split guide member according to an exemplary embodiment of the present invention;

FIGS. 34A-34C illustrate in detail the center torque tube of according to an exemplary embodiment of the present invention;

DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The systems disclosed herein boast a variety of inventive features and components that warrant patent protection, both individually and in combination.

Figure 1:
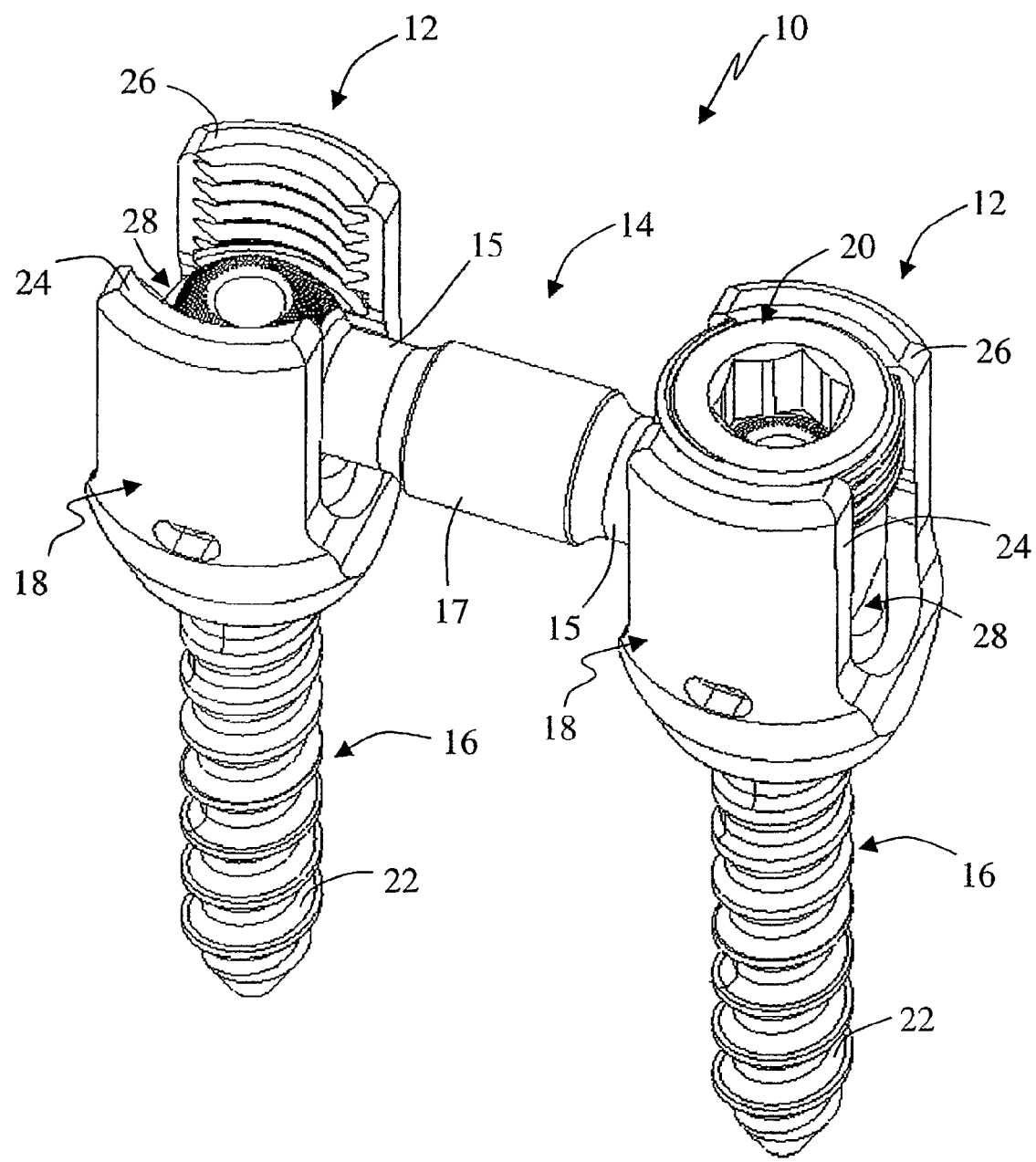
FIG. 1 is a perspective view of a "single level" spinal fixation system for use according to the present invention, including (by way of example only) first and second pedicle screws and a connecting element having dual shaped portions on either end.
Figure 2:
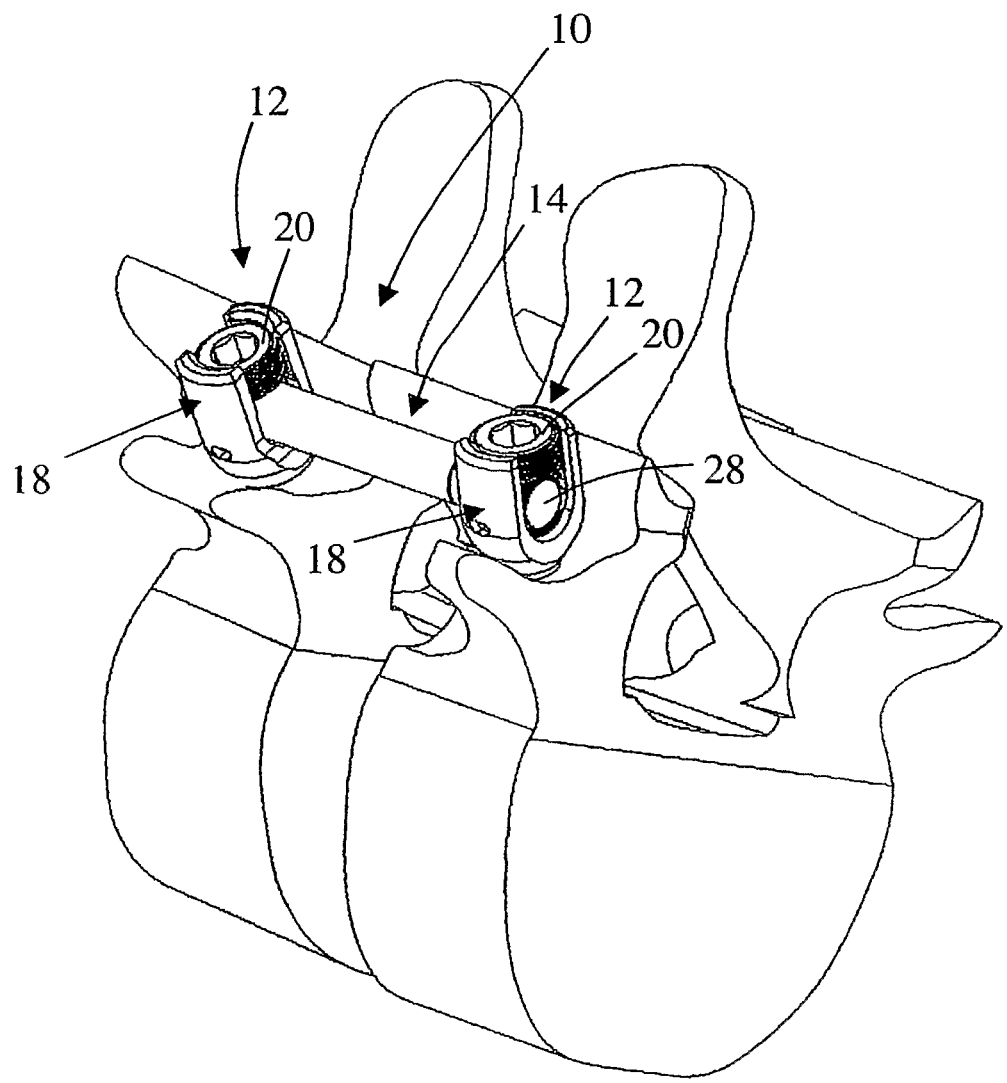
FIG. 2 is a perspective view of a "single level" spinal fixation system in use according to the present invention, including (by way of example only) first and second pedicle screws and a connecting element having dual shaped portions on either end.
Figure 3:
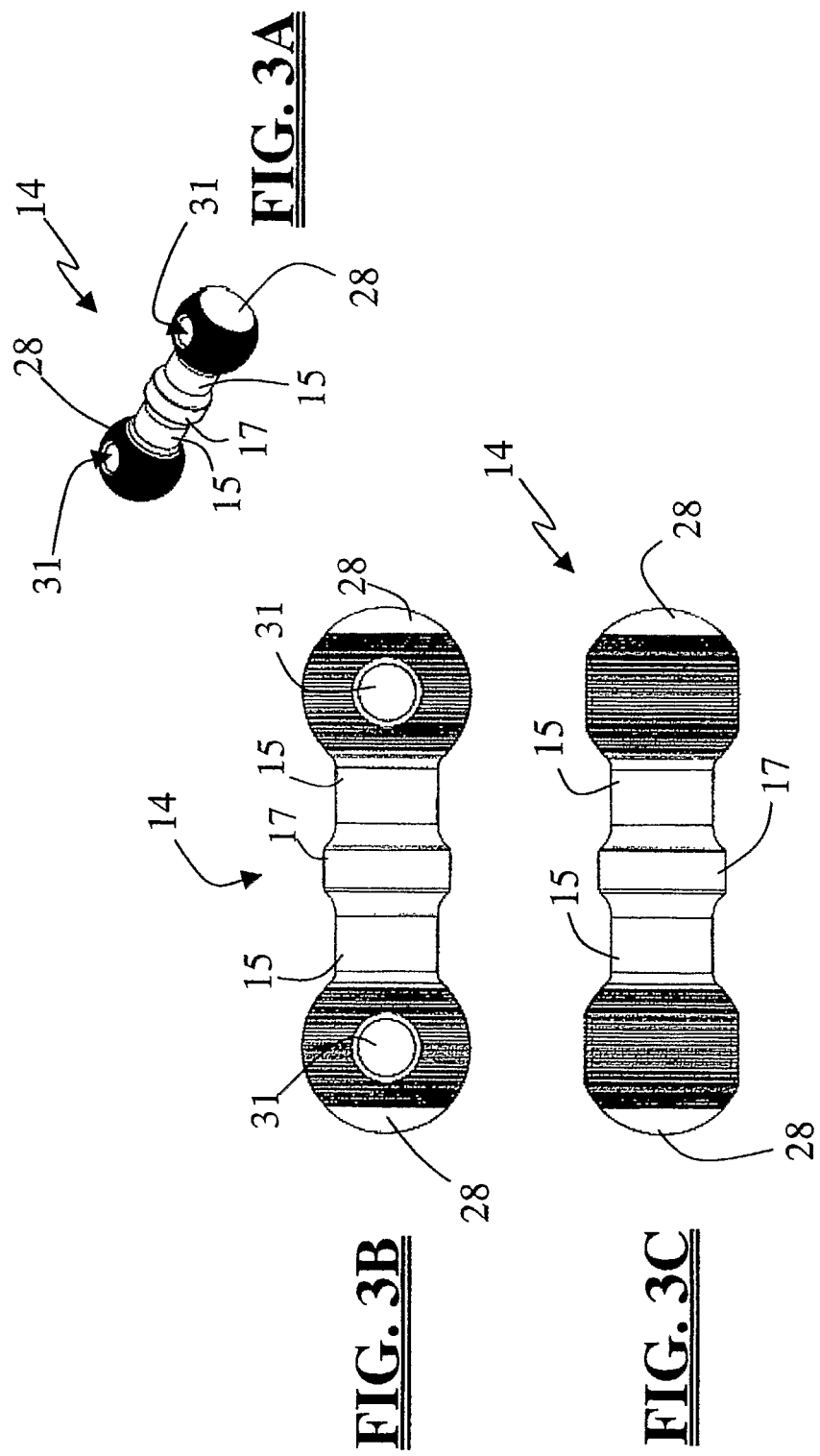
FIGS. 3A-3C illustrate an elongated connecting element having shaped ends for use in a single level fixation according to the present invention.
Figure 4:
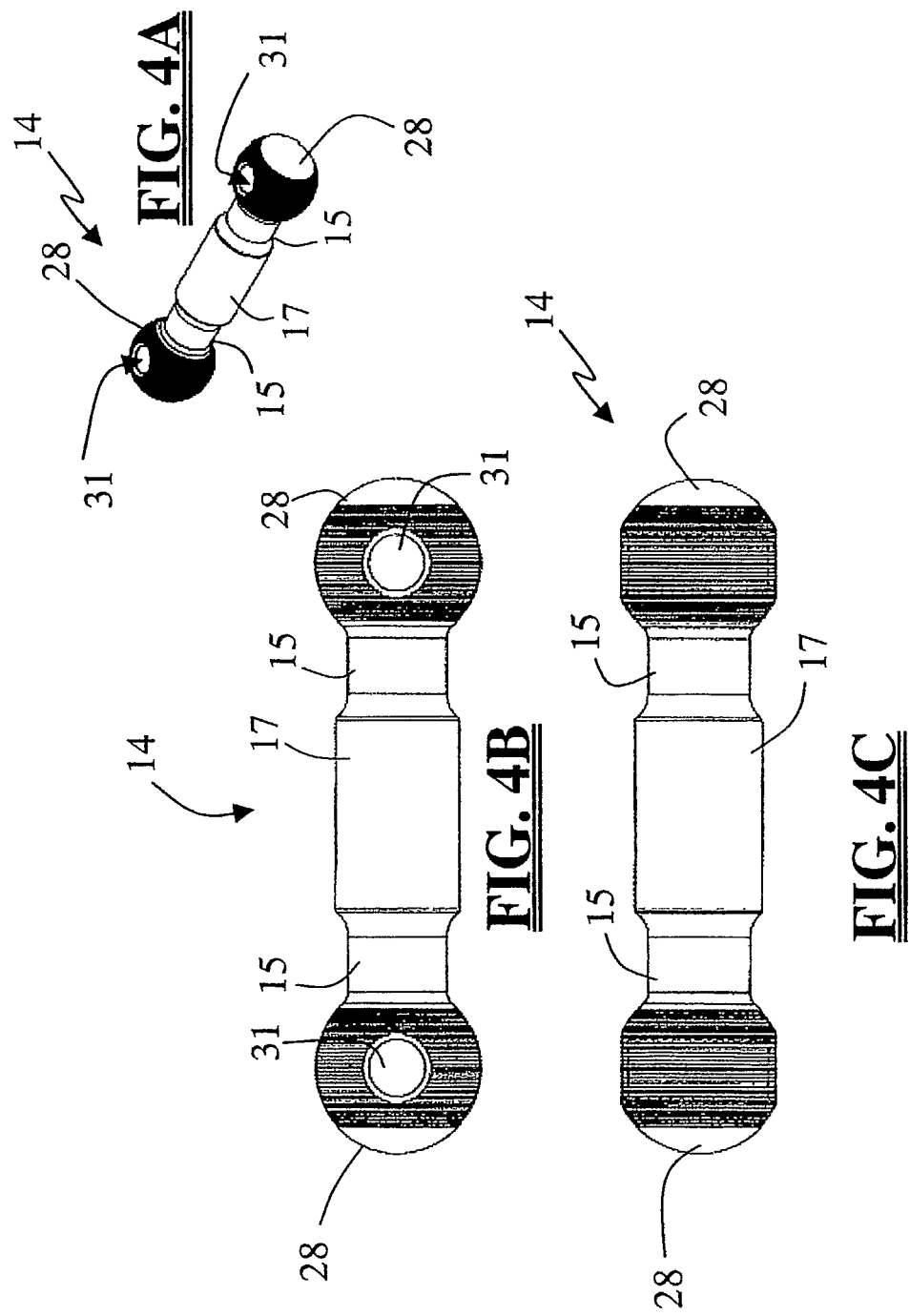
FIGS. 4A-4C illustrate another embodiment of an elongated connecting element having shaped ends for use in a single level fixation.

FIGS. 1 and 2 illustrate a spinal fixation system 10 according to the "single level" embodiment of the present invention. The spinal fixation system 10 includes a pair of pedicle screw assemblies 12 and a generally elongate connecting element 14 having shaped ends 28. By way of example only, the pedicle screw assemblies 12 are poly-axial in nature, with a screw member 16, a housing 18, and a locking screw 20, of the type shown and described in commonly owned and co-pending U.S. patent application Ser. No. 11/031,506 entitled "System and Method for Performing Spinal Fixation" filed Jan. 6, 2005 ("the '506 application"), the entire contents of which is hereby incorporated by reference as if set forth fully herein. The screw member 16 and housing 18 are separate articles such that the angle of the housing 18 relative to the screw member 16 may be varied in any number of fashions prior to locking them together, hence the term "poly axial" to describe this type of pedicle screw assembly 12 according to the present invention. The screw member 16 includes a thread 22 suitable for introduction into and purchase within bone. Each housing 18 includes first and second branches 24, 26, which collectively form a generally "U-shaped" structure defining or containing an area dimensioned to receive the shaped end 28 formed either end of the connecting element 14 (according to one aspect of the present invention) and thereafter the locking screw 20. In a preferred aspect, each component of the poly-axial pedicle screw assembly 12 is cannulated (i.e. it is equipped with a longitudinal lumen extending through the locking screw 20 and screw member 16) such that a K-wire may be used to guide the poly-axial pedicle screw assembly 12 into the patient according to the present invention.

FIGS. 3A-3C and 4A-4C illustrate various connecting elements 14 for use in the "single level" embodiment of the present invention. In addition to the shaped ends 28, each connecting element 14 includes two neck regions 15 extending between a central region 17 and the shaped ends 28. The shaped ends 28 are generally spherical and include an aperture or cannulation 31 capable of receiving a guide wire therethrough. It will be appreciated that, although shown as generally spherical and cannulated, the shaped ends 28 may be partially spherical, non-cannulated, and/or comprise any form or shape capable of being disposed wholly within the housing 18 of the pedicle screw assembly 12, including but not limited to the generally spherical shape shown and described herein and in the '506 application, as well as the non-spherical shaped ends disclosed in commonly owned and co-pending U.S. patent application Ser. No. 10/894,533 ("the '533 application"), the entire contents of which are incorporated by reference as if set forth fully herein. Connecting element 14 may be provided having any of a range of suitable dimensions to accommodate the anatomical and pathologic considerations of the given patient for a single level application, including but not limited to a length (including the shaped ends 28) ranging from 15 mm to 25 mm. Although shown as generally straight, it will be appreciated that the connecting element 14 may be curved slightly (particularly for the larger sizes) to better accommodate the natural curvature of the spine over a single level.

As will be described in greater detail below, the feature of providing shaped ends 28 on the connecting element 14 avoids the "overhang" prevalent with prior art pedicle systems which employ straight rods as connecting elements (without shaped ends). This feature is also advantageous in that it provides the ability to rotate the housing 18 of the poly-axial pedicle screw assemblies 12 about the shaped end 28 to accomplish "instrument free" compression and/or distraction via the use of the introduction devices forming part of the present invention (described below) as opposed to separate and distinct compression and/or distraction instruments. This, it will be appreciated, saves valuable operative time in eliminating the use of dedicated compression and/or distraction tools, as well as the associated cost of manufacturing and providing such dedicated compression and/or distraction instruments.

Figure 5:
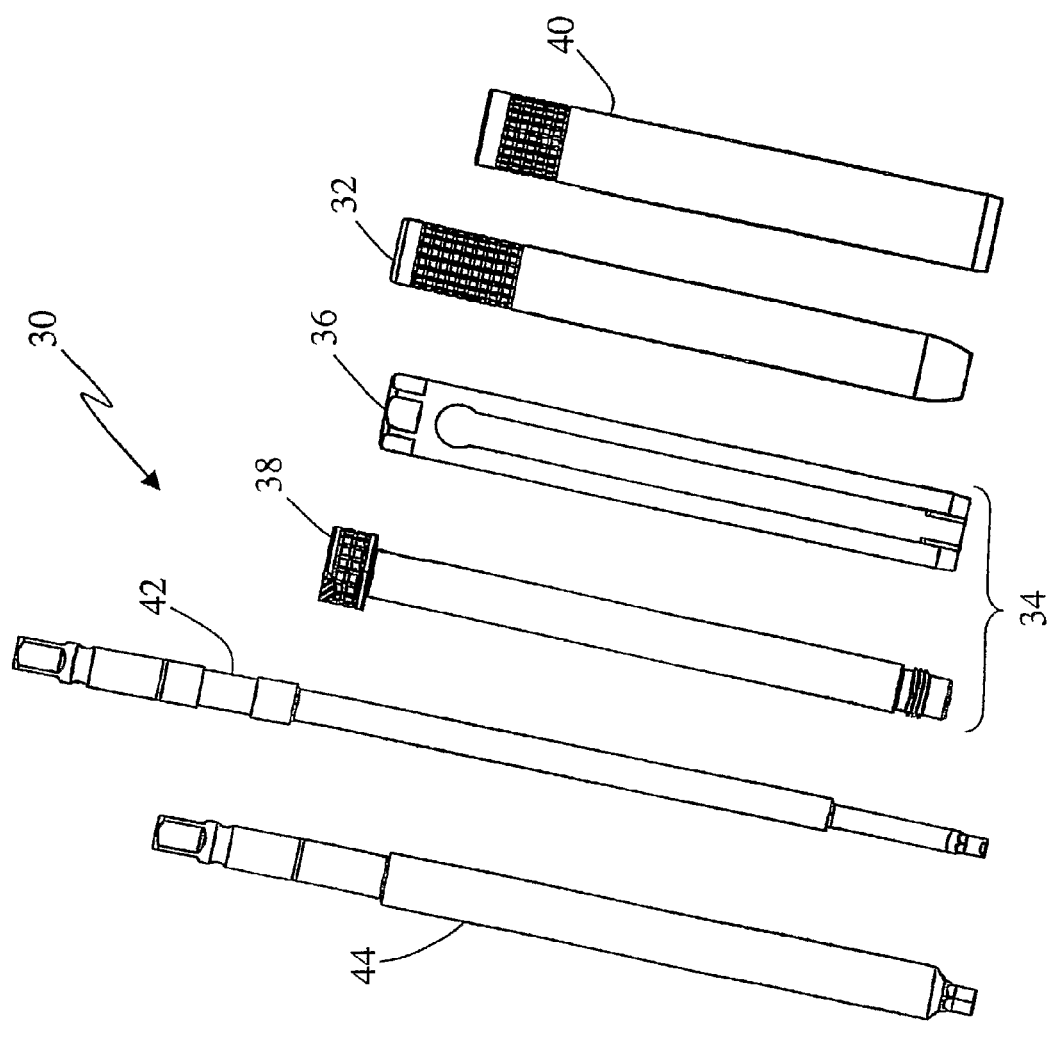
FIG. 5 illustrates a system for surgically introducing the "single level" spinal fixation system of FIG. 1 in a minimally invasive fashion, including (By way of example) a tap insulator, guide assembly (comprising a guide member and an inner sleeve), guide assembly insulator, pedicle screw driver, and a lock screw driver.
Figures 7A, 7B:
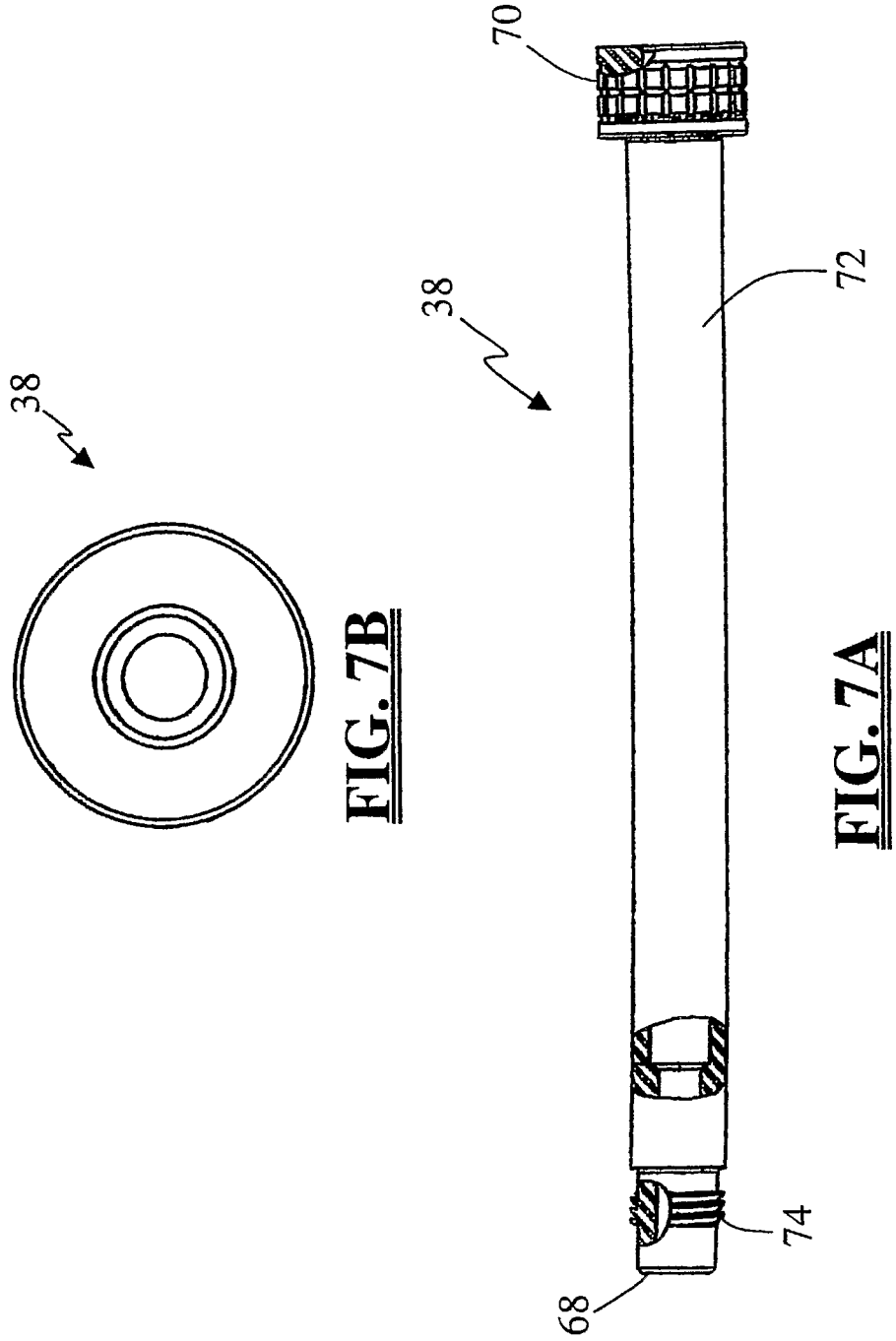
FIG. 7A-7E illustrate in detail various aspects of the inner sleeve forming part of the guide assembly according to one exemplary embodiment of the present invention.
Figure 7E:
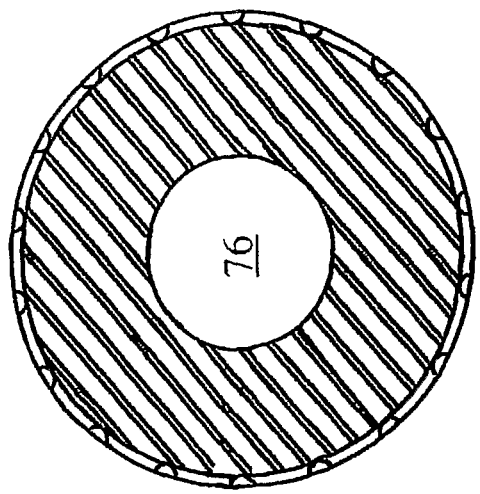
Figure 7D:
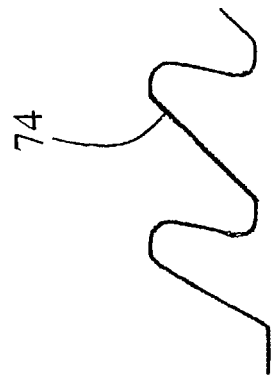
Figure 7C:
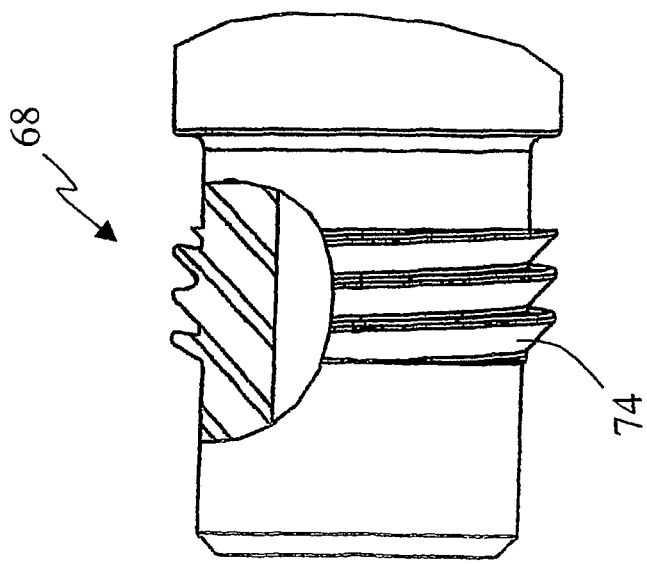

FIG. 5 illustrates a minimally disruptive introduction system 30 for introducing the spinal fixation system 10 according to the "single level" embodiment of the present invention. The introduction system 30 includes (by way of example only) a tap insulator 32, a guide assembly 34 (comprising a guide member 36 and an inner sleeve 38), a guide assembly insulator 40, a pedicle screw driver 42, and a lock screw driver 44. In addition to the instruments shown, the introduction system 30 may also include a spinal access needle for accessing a pedicle target site (e.g. Jamshidi needle), a guide wire (e.g. K-wire) for placement through the spinal access needle and creating an initial hole in the pedicle target site, a guide wire insulator for insulating the guide wire during optional EMG-based pedicle integrity testing during the guide wire introduction process, and a cannulated tap for advancement over the guide wire to prepare a tapped pilot hole. The individual components of the introduction system 30 will be described in detail with reference to FIGS. 5-11 and the use of the introduction system 30 with the spinal fixation system 10 will be described with reference to FIGS. 12-28.

In general, however, the guide assembly 34 is dimensioned to introduce (as a first step) each pedicle screw 12 into a target pedicle site—preferably with the assistance of the pedicle screw driver 42—and (as a second step) guide the shaped ends 28 of the connecting element 14 into the receiving area of the pedicle screw housing 18. Following that, the locking element driver 44 may be employed to secure the locking element 20 within the pedicle screw housing 18 to thereby lock the connecting element 14 to the pedicle screw assembly 12. The tap insulator 32 and guide assembly insulator 40 may be employed during optional EMG-based pedicle integrity testing, such as shown and described in commonly owned and co-pending U.S. patent application Ser. No. 11/061,184 entitled "Systems and Methods for Performing Dynamic Pedicle Integrity Assessments" filed Feb. 18, 2005 and U.S. patent application Ser. No. 10/836,105 entitled "Systems and Methods for Performing Percutaneous Pedicle Integrity Assessments filed Apr. 30, 2004 ("the NeuroVision Applications"), the entire contents of which are hereby incorporated by reference as if set forth fully herein.

FIGS. 6A-6C illustrate in detail various aspects of the guide member 36 forming part of the guide assembly 34 according to an exemplary embodiment of the present invention. Guide member 36 has a generally elongated cylindrical shape with a length sufficient to extend from a pedicle target site at a distal end 56, to a position outside the surgical corridor at a proximal end 58, as best viewed in FIG. 20. An interior lumen 60 extends from distal end 56 to proximal end 58. The guide member 36 includes a guide channel 64 having an enlarged keyhole opening 66 at a proximal end and an open distal end.

In a significant aspect of the present invention, the guide channel 64 passes into the interior lumen 60 and extends substantially along the guide from distal end 56 to a position short of proximal end 58. The keyhole opening 66 is dimensioned to receive the shaped end 28 of connecting element 14 such that the shaped end 28 will be disposed within the interior lumen 60. Once the shaped end 28 is received into the interior lumen 60, the neck portion 15 of the connecting element 14 may pass through the guide channel 64 such that the shaped ends 28 may be advanced into engagement within the pedicle screw housing 18. The shaped end 28 is provided having a diameter that is larger than the width of the guide channel 64, such that the shaped end 28 is retained within the interior lumen 60 during this process.

Guide member 36 preferably comprises a surgical grade metal such as, by way of example, stainless steel, aluminum and/or titanium, although other biologically suitable compositions (such as, by way of example, plastics, ceramics, and/or carbon composites) may be employed as well. The guide member 36 may be provided having any number of suitable dimensions to accommodate the anatomical and pathologic considerations of the given patient, including but not limited to a length ranging from 4 to 6 inches.

FIGS. 7A-7E illustrate in detail various aspects of the inner sleeve member 38 forming part of the guide assembly 34 according to an exemplary embodiment of the present invention. Inner sleeve member 38 has a generally elongated cylinder shape with a distal end 68, a proximal end 70, and a center region 72. Distal end 68 includes a threaded region 74 for engaging a corresponding threaded region within screw housing 18 of pedicle screw 12, thereby coupling pedicle screw 12 to the guide assembly for insertion into the pedicle target site. Center region 72 is dimensioned to extend through interior lumen 60 of guide member 36 such that distal end 68 may engage with screw housing 18 when fully inserted. Proximal end 70 has a circumference generally greater than center region 72 and may not pass into interior lumen 60 of guide member 36. Proximal end 70 may also include knurling to increase operator control. Inner sleeve 38 also includes an interior lumen 76 extending from distal end 68 to proximal end 70 and dimensioned to receive the pedicle screw driver 42 for the purpose of tightening the pedicle screw assembly 12 prior to introducing the shaped end 28 of the connecting element 14 into the housing 18.

FIGS. 8A-8E illustrate in detail various aspects of the pedicle screw driver 42 according to an exemplary embodiment of the present invention. Screw driver 42 is dimensioned to be inserted through the inner sleeve member 38 of guide assembly 34. A distal end 84 (FIGS. 8D-8E) is configured to engage screw member 16 of pedicle screw 12. A proximal end 86 (FIGS. 8B-8C) is configured to engage and attach to any of a variety of suitable handles. Pedicle screw driver 42 may preferably include an interior lumen 88 (FIG. 8D-8E) extending from distal end 84 to proximal end 86 to allow insertion over a guide wire (not shown).

FIGS. 9A-9E illustrate in detail various aspects of the lock screw driver 44 according to an exemplary embodiment of the present invention. Lock screw driver 44 is dimensioned to be inserted through the interior lumen 60 of guide member 36. A distal end 90 (FIGS. 9D-9E) is configured to engage a receiving area within the lock screw 20 of spinal fixation system 10. A proximal end 92 (FIGS. 9B-9C) is configured to engage and attach to any of a variety of suitable handles.

FIGS. 10A-10E illustrate in detail various aspects of the tap insulator 32 according to one exemplary embodiment of the present invention. Tap insulator 32 has a generally elongated cylinder shape with a length sufficient to extend from a vertebral pedicle at a distal end 50, to a position outside the surgical corridor at a proximal end 52, as best viewed in FIGS. 14-15. The tap insulator 32 is provided with an interior lumen 54 (FIGS. 10B, 10E) extending from the distal end 50 to the proximal end 52, which is dimensioned to allow passage of a tap (preferably cannulated) to a pedicle target site. Tap insulator 32 is designed to insulate tissue from electrical signals passed through the tap (not shown) during optional EMG-based pedicle integrity testing during tapping, as set forth in greater detail in the NeuroVision Applications. Tap insulator 32 accomplishes this by being constructed of any number of suitable non-conductive materials, including but not limited to a durable plastic such as, by way of example, Raedel, and/or surgical grade metal (such as, by way of example, aluminum or titanium) with an insulating coating. The tap insulator 32 may be provided having any number of suitable dimensions to accommodate the anatomical and pathologic considerations of the given patient, including but not limited to a length ranging from 4 to 7 inches. Distal end 50 (FIG. 10D) may be tapered to minimize tissue impaction during insertion and proximal end 52 (FIG. 10C) may include knurling to increase operator control over the instrument.

FIGS. 11A-11E illustrate in detail various aspects of the guide insulator 40 according to an exemplary embodiment of the present invention. Guide insulator 40 has a generally elongated cylinder shape with a length sufficient to extend from a vertebral pedicle at a distal end 78, to a position outside the surgical corridor at a proximal end 80, as best viewed in FIG. 19. Guide insulator 40 is provided with an interior lumen 82 (FIGS. 11B, 11E) extending from distal end 78 to proximal end 80. The lumen 82 is dimensioned to allow guide assembly 34 to extend through to the pedicle target site and to allow guide insulator 40 to be passed over the exterior surface of tap insulator 32 to the pedicle target site. Guide insulator 40 is designed to insulate tissue from electrical signals passed through the driver and pedicle screw (not shown) during optional EMG-based pedicle integrity testing during screw placement, as set forth in greater detail in the NeuroVision Applications. Guide insulator 40 accomplishes this by being constructed of any number of suitable non-conductive materials, including but not limited to a durable plastic such as, by way of example, Raedel, and/or surgical grade metal (such as, by way of example, aluminum or titanium) with an insulating coating. The guide insulator 40 may be provided having any number of suitable dimensions to accommodate the anatomical and pathologic considerations of the given patient, including but not limited to a length ranging from 4 to 7 inches. Proximal end 80 may include knurling to increase operator control over the instrument.

Figure 12:
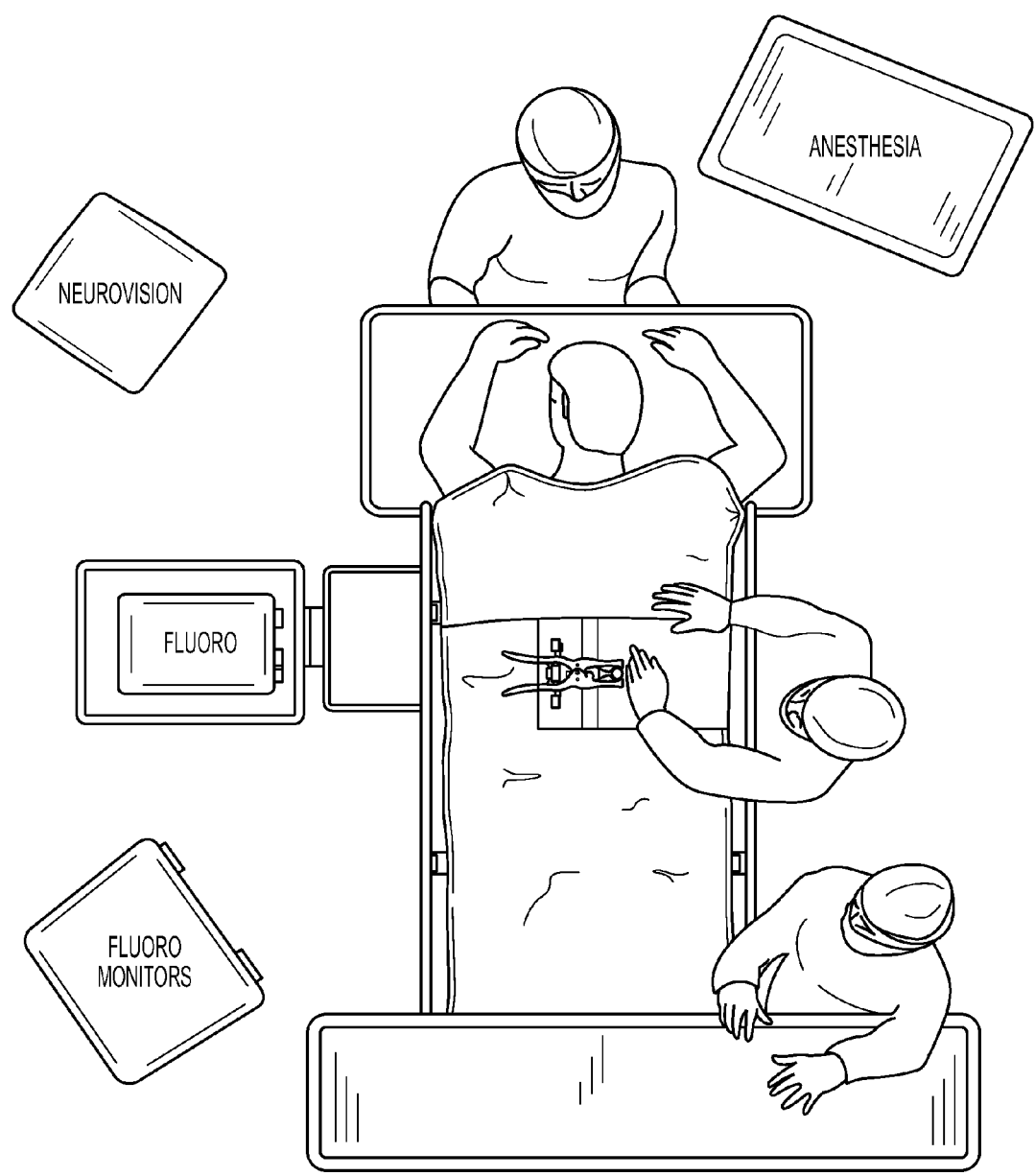
FIG. 12 is an overhead view of a first step in employing the spinal fixation system of FIG. 1 and the minimally invasive insertion system of FIG. 5, including (by way of example), preparing the OR, placing the patient on the operating table, and making the desired incisions.
Figure 13:
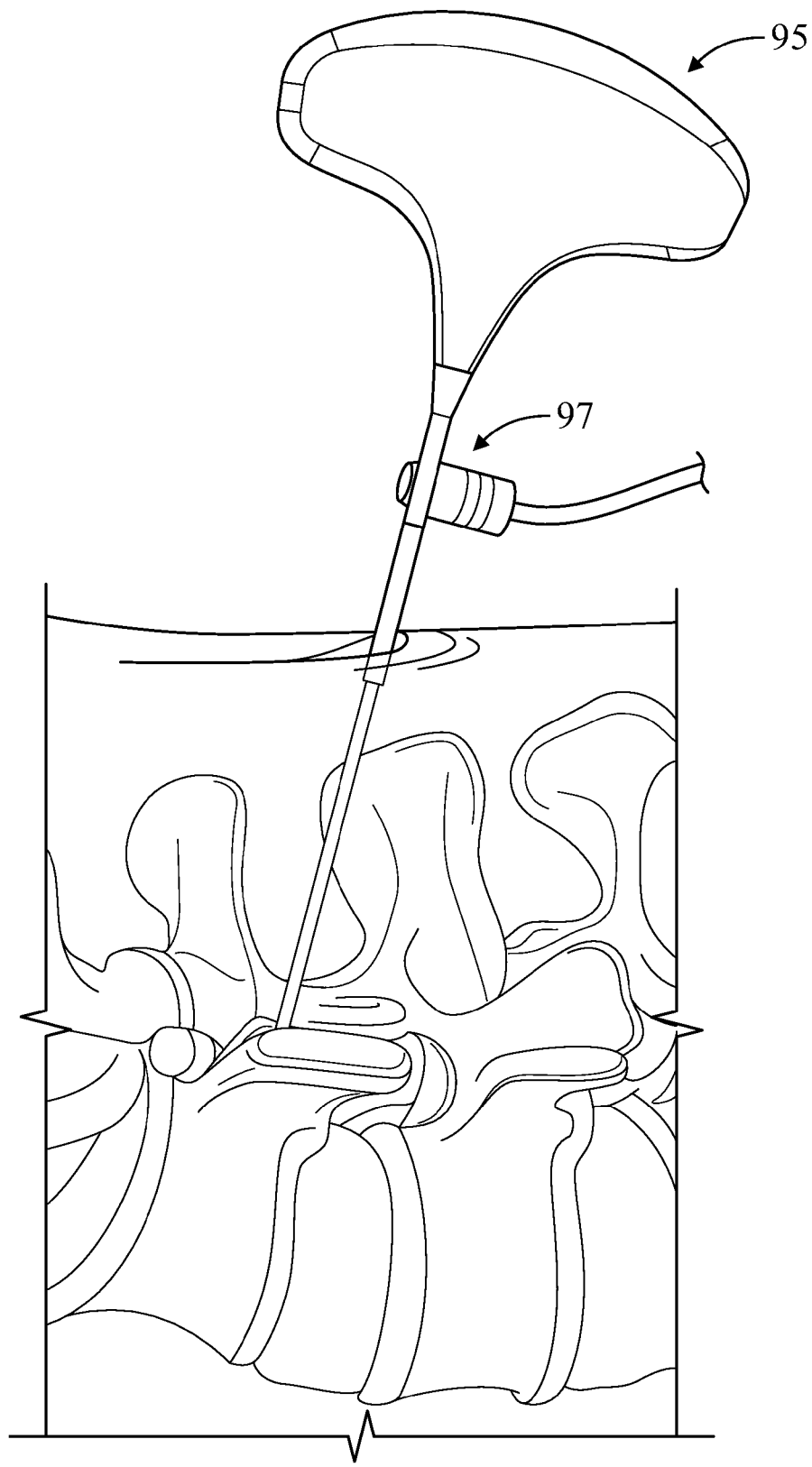
FIG. 13 illustrates a method of accessing a pedicle target site with a Jamshidi needle (and optional EMG based pedicel integrity testing) during the minimally invasive insertion of the spinal fixation system of FIG. 1 according to an exemplary embodiment of the present invention.
Figure 14:
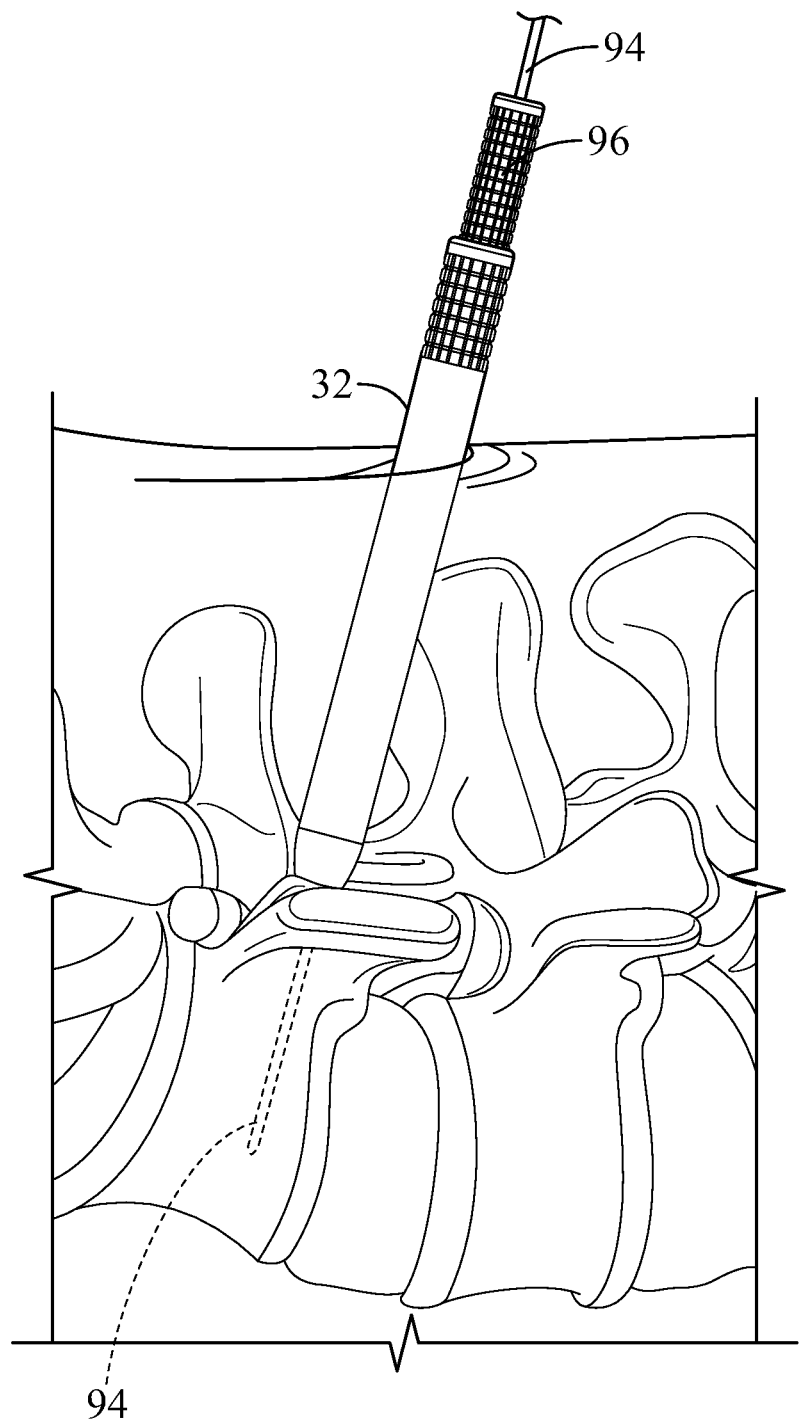
FIG. 14 illustrates the tap insulator of FIG. 10 in use during the minimally invasive insertion of the spinal fixation system of FIG. 1 according to an exemplary embodiment of the present invention.

The spinal fixation system 10 and minimally disruptive introduction system 30 of the "single level" embodiment of the present invention system may be employed as follows. According to one embodiment, as illustrated in FIG. 12, a first step involves placing a patient on an operating table, preferably in the prone position, and thereafter making small incisions over the desired vertebra. A pedicle target site may then be accessed and a pilot hole formed using a spinal access needle 95 (ie. Jamshidi needle), as shown in FIG. 13. Optional EMG-based pedicle integrity testing may be performed at this stage by coupling a non-insulated portion of the spinal access needle 95 to a clip 97 to establish electrical communication with a neuromonitoring system of the type in the NeuroVision Applications. The spinal access needle 95 is preferably insulated along the shaft such that the electrical signals selectively transmitted to the spinal access needle via the neuromonitoring system are transmitted at or near the distal end of the access needle 95. This avoids shunting the electrical signals into the tissue of the patient, and focuses the electrical stimulation at the working end of the spinal access needle 95. If the spinal access needle 95 breaches the pedicle, the electrical stimulation will transmit through the hole or breach and stimulate adjacent neural elements. By monitoring the degree of this evoked response, the surgeon may assess if the integrity of the pedicle has been breached during pilot hole formation.

Once the pilot hole has been formed, a guide wire 94 (e.g. K-wire) may then be inserted into the pedicle through a cannulation formed in the pedicle access needle 95. The pedicle access needle 95 may thereafter be carefully removed such that only the K-wire 94 remains in the pilot hole. In the next step, shown in FIG. 14, a K-wire insulator 96 (of the type disclosed in the NeuroVision Applications) may be inserted over the K-wire 94 and then the tap insulator 32 may be inserted over the K-wire insulator 96, both while performing optional EMG-based pedicle integrity testing as described in the NeuroVision Applications.

Figure 15:
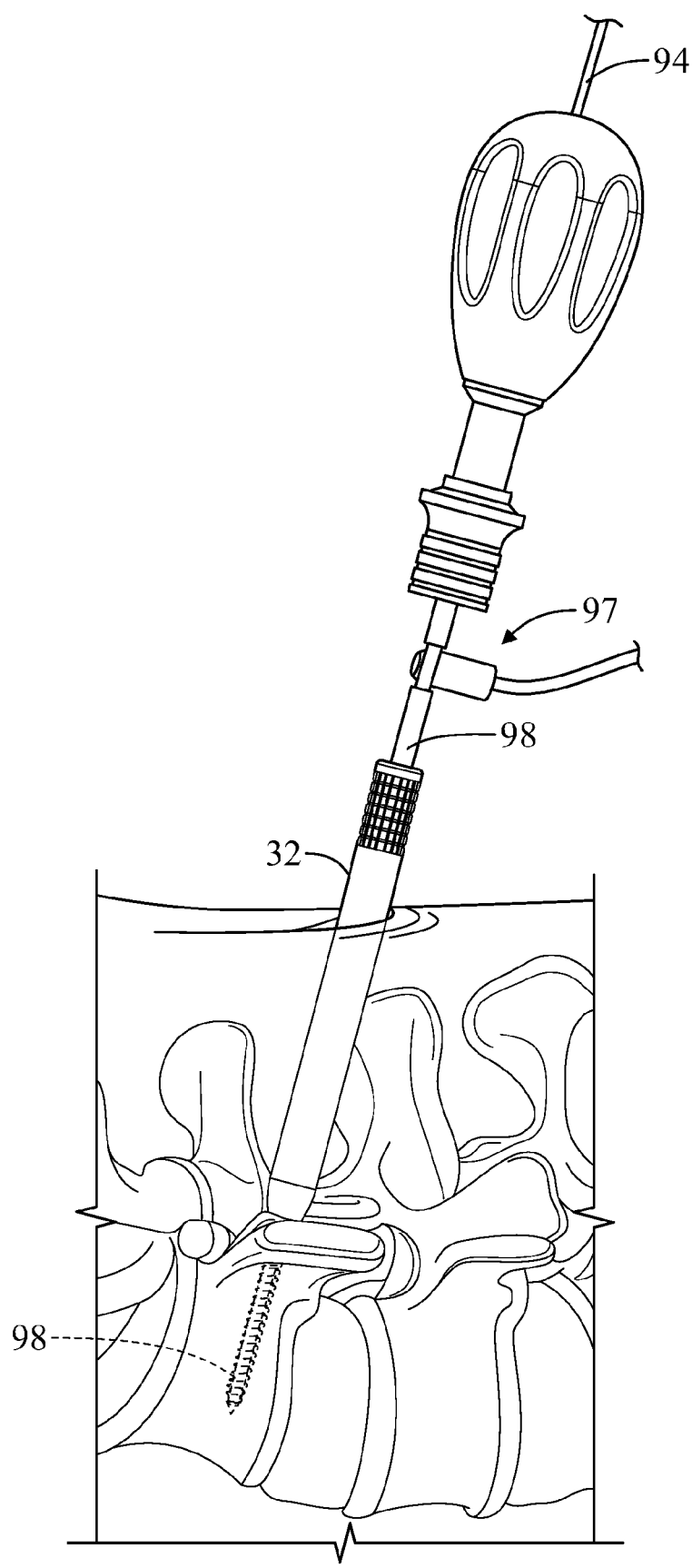
FIG. 15 illustrates the tap insulator of FIG. 10 in combination with a tap (and optional EMG based integrity tester) during the minimally invasive insertion of the spinal fixation system of FIG. 1 according to an exemplary embodiment of the present invention.

The next step, shown in FIG. 15, involves tapping the previously formed pilot hole. A cannulated tap 98 is inserted over the K-wire 94 and through the tap insulator 32 to the pedicle target site. The pilot hole may then be tapped while performing optional EMG-based pedicle integrity testing as described in the NeuroVision Applications in order to detect any breach in the pedicle caused during the tapping process. If the pedicle integrity assessment is positive (meaning a high stimulation threshold), then pilot hole preparation may be considered complete and the tap 98 removed from the tap insulator 32. This procedure may be repeated to prepare a pilot hole for each pedicle in which a pedicle screw assembly 12 will be placed.

Figure 16:
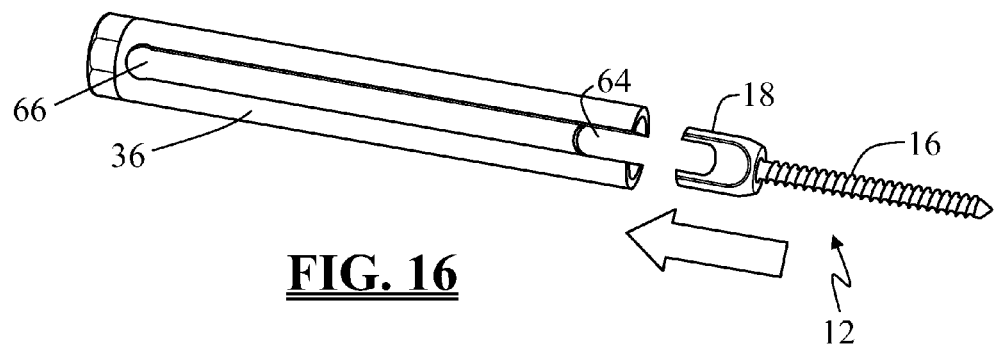
FIGS. 16-18 illustrate the method of preparing a pedicle screw and the guide assembly of FIG. 5 for minimally invasive insertion according to an exemplary embodiment of the present invention.
Figure 17:
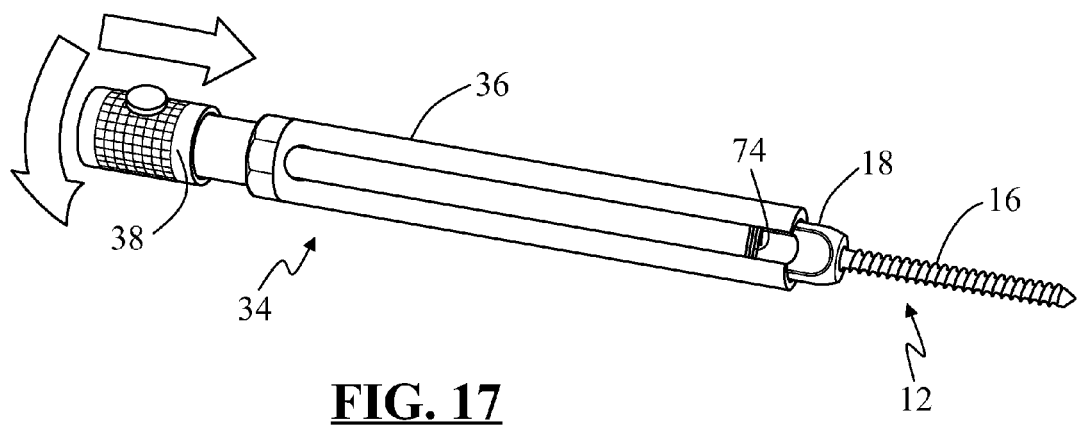
Figure 18:
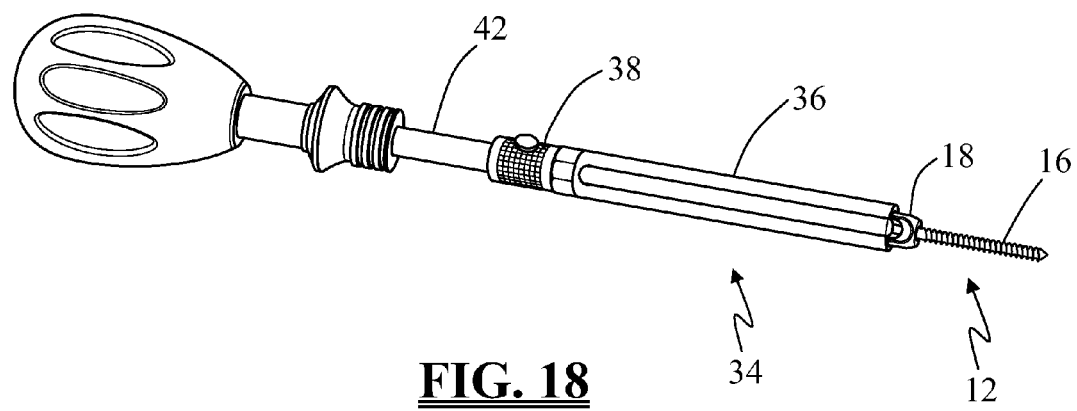
Figure 19:
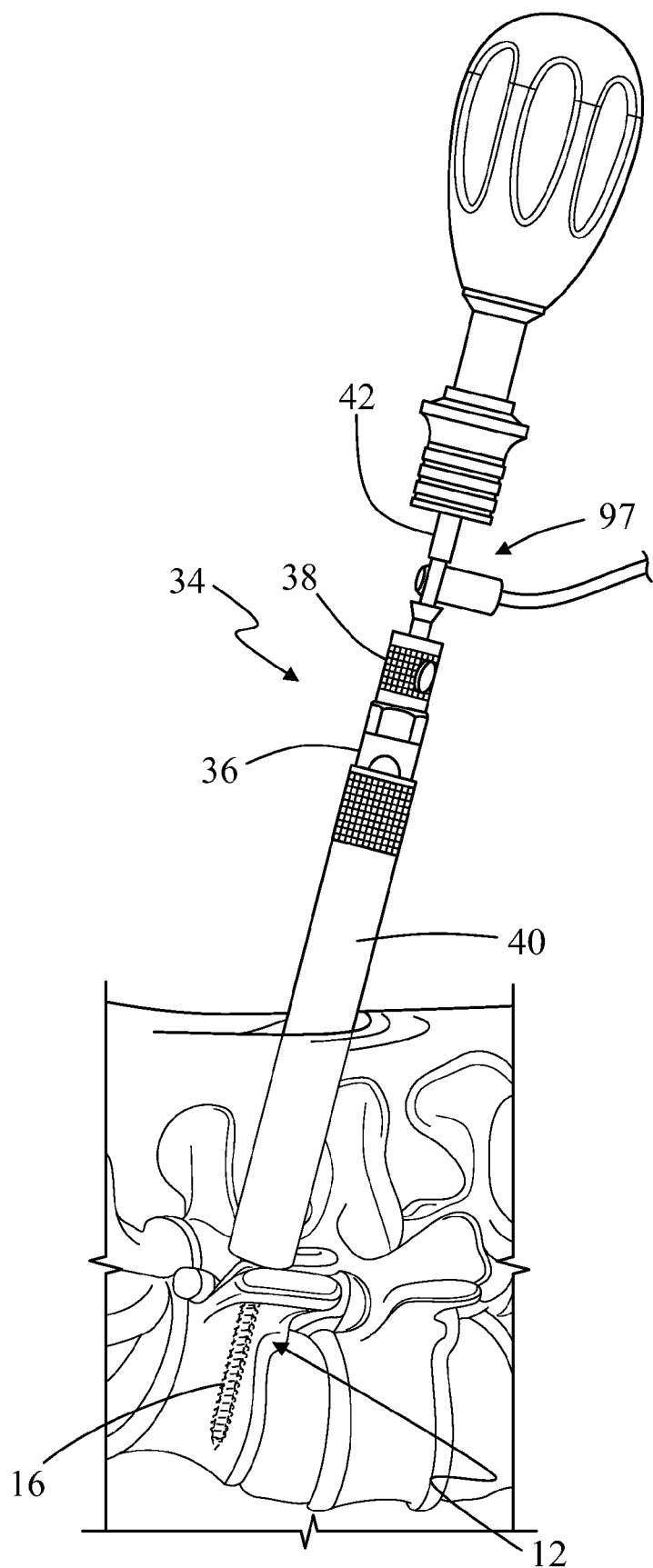
FIG. 19 illustrates the minimally invasive insertion of the a pedicle screw using the minimally invasive insertion system of FIG. 5 according to an exemplary embodiment of the present invention.

FIGS. 16-18 illustrate the method of preparing a pedicle screw assembly 12 and the guide assembly 34 for use in pedicle screw placement according to one embodiment of the present invention. The screw housing 18 of pedicle screw assembly 12 is inserted into the distal end of guide member 36 as shown in FIG. 16. The next step, shown in FIG. 17, involves inserting inner sleeve member 38 through the guide member 36 such that the threaded region 74 of inner sleeve member 38 is engaged with a corresponding threaded region in screw housing 18. At this point, as best viewed in FIG. 18, the pedicle screw driver 42 is then inserted through the inner sleeve member 38 and engaged into a receiving area within the proximal end of the screw member 16 of pedicle screw assembly 12. Once the pedicle screw assembly 12 is coupled to the guide assembly 34, the surgeon may undertake to place the pedicle screw assembly 12 into a pedicle according to the present invention.

Figure 20:
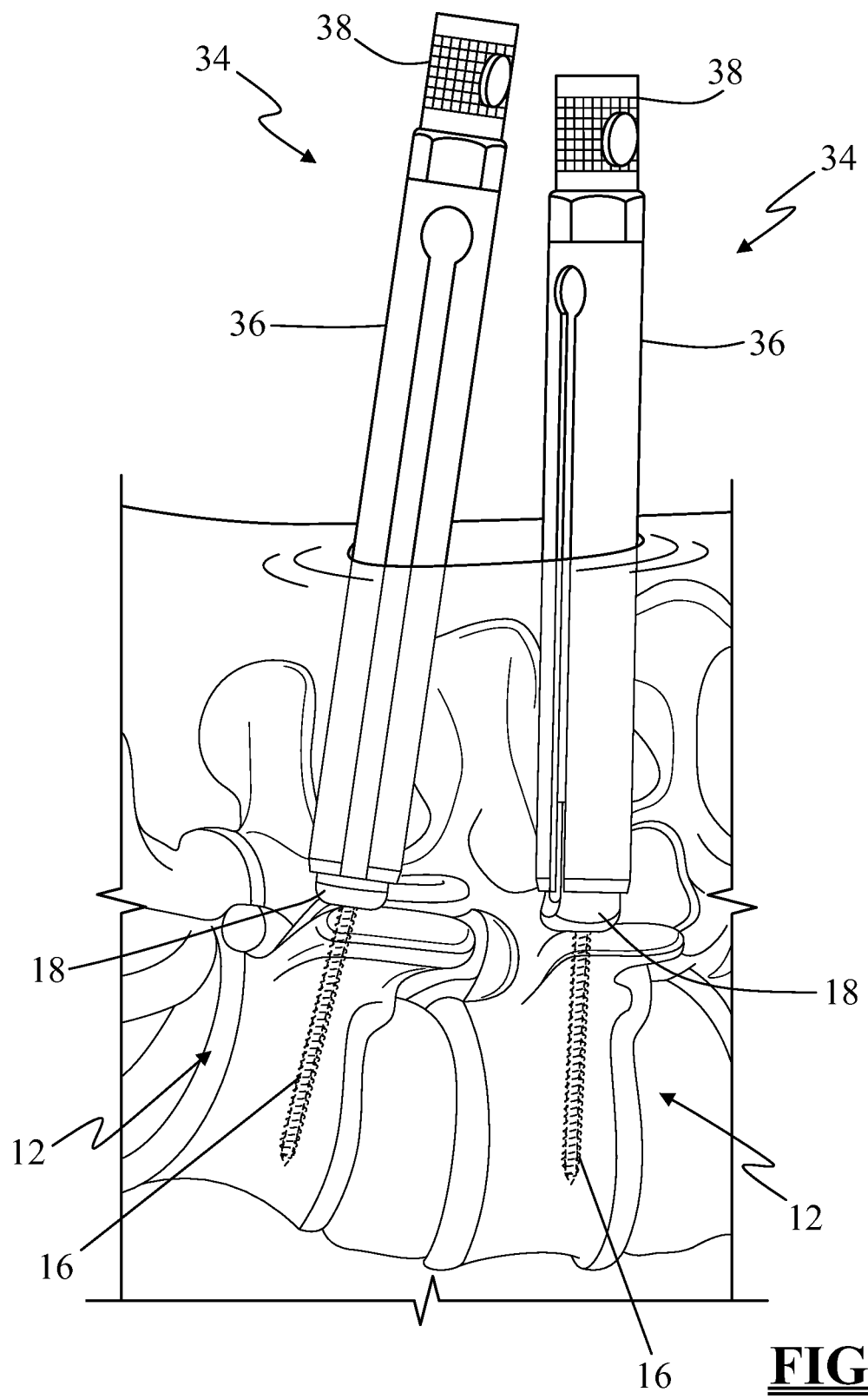
FIG. 20 is an illustration of the guide assembly after screw insertion is complete and the screw driver has been removed.

To prepare for screw insertion according to a preferred embodiment of the present invention, the guide insulator 40 is first inserted to the pedicle target site over the tap insulator 32. With the guide insulator 40 in place, the tap insulator 32 (and tap 98, if still present inside the insulator 32) may then be removed. The guide assembly 34 with the pedicle screw assembly 12 coupled thereto may then be placed over the K-wire 94 and inserted to the pedicle target site through the guide insulator 40, illustrated in FIG. 19, preferably while performing optional EMG-based pedicle integrity testing as described in the NeuroVision Applications to monitor for potential pedicle breaches during screw placement. Once the pedicle screw assembly 12 is safely introduced into the respective pedicle target site, then the pedicle screw driver 42 and guide insulator 40 may be removed so as to leave only the guide assembly 34 in place, as shown in FIG. 20. This process may be repeated for each pedicle screw assembly 12 to be placed.

Figure 21:
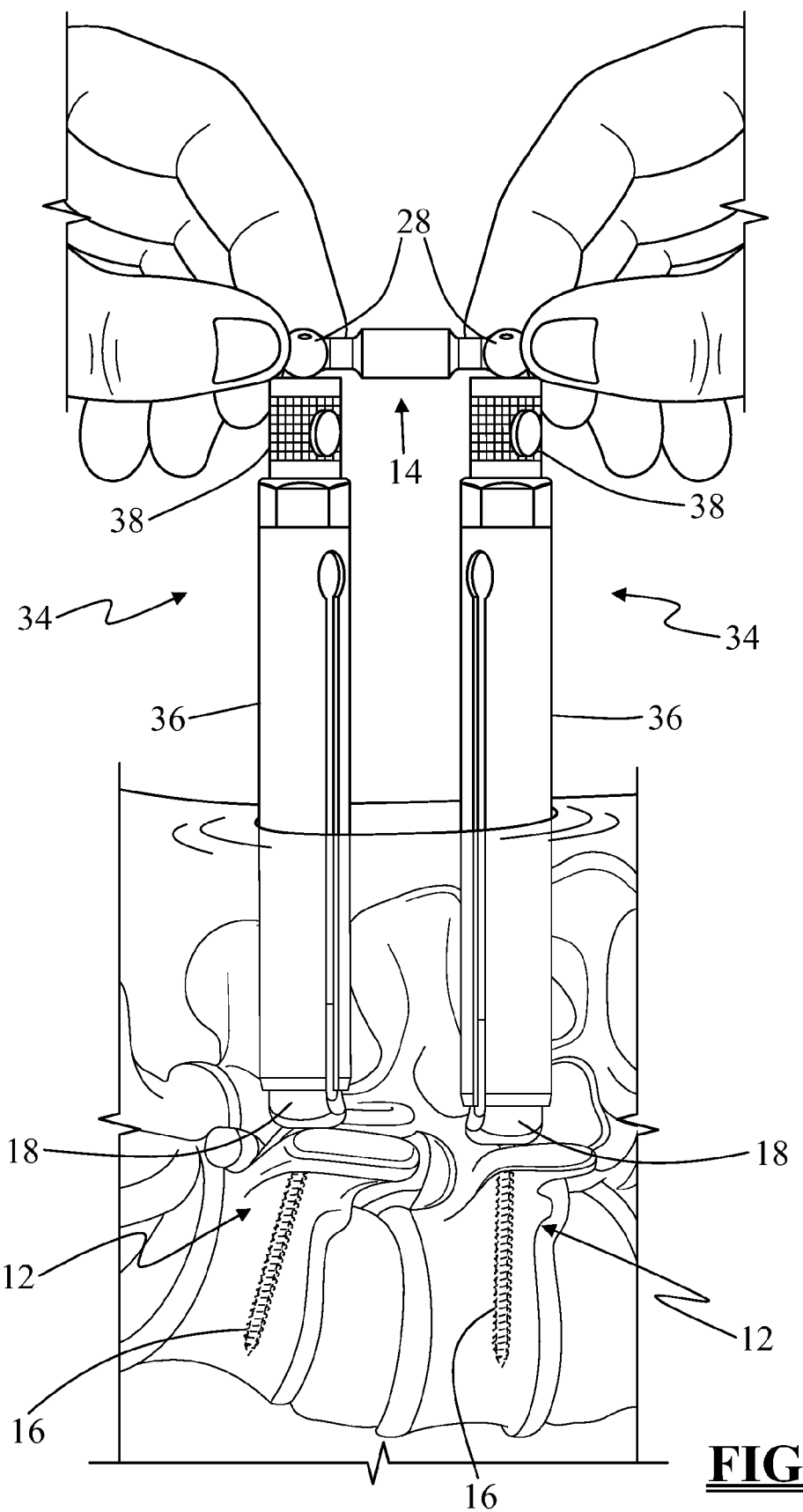
FIG. 21 illustrates a method of selecting an appropriately sized connecting element according to an exemplary embodiment of the present invention.
Figure 22:
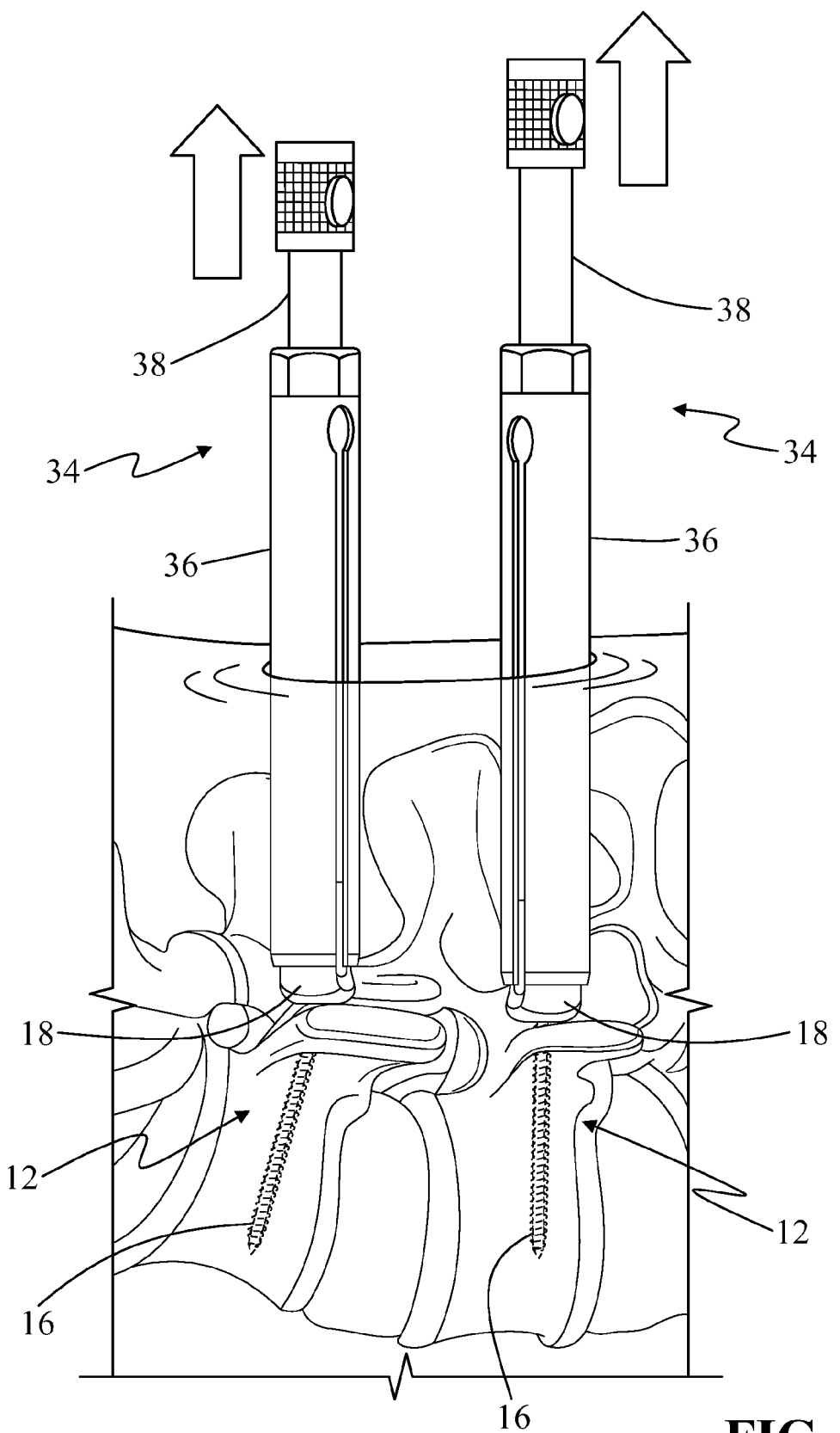
FIG. 22 illustrates the removal of the inner sleeve members during the minimally invasive insertion of the spinal fixation system of FIG. 1 according to an exemplary embodiment of the present invention.

Turning to FIG. 21, with the pedicle screw assemblies 12 and guide assemblies 34 in place, the surgeon may then select a connecting element 14 of appropriate size. In one embodiment, the connecting element 14 may be selected by matching it to the length of the guide assemblies 34 after they have been brought into a generally parallel arrangement as shown. Slightly longer or slightly shorter connecting elements 14 may be selected based the experience and particular needs of the surgeon. By way of example only, a longer connecting element 14 may be selected if extra distraction is desired and/or a shorter connecting element 14 may be selected if extra compression is desired. Once the appropriate size connecting element 14 has been selected, the inner sleeve members 38 may then be unthreaded from each screw housing 18 and removed from the guide member 36 as shown in FIG. 22, taking care not to dislodge the guide member 36 from the screw housing 18.

Figure 23:
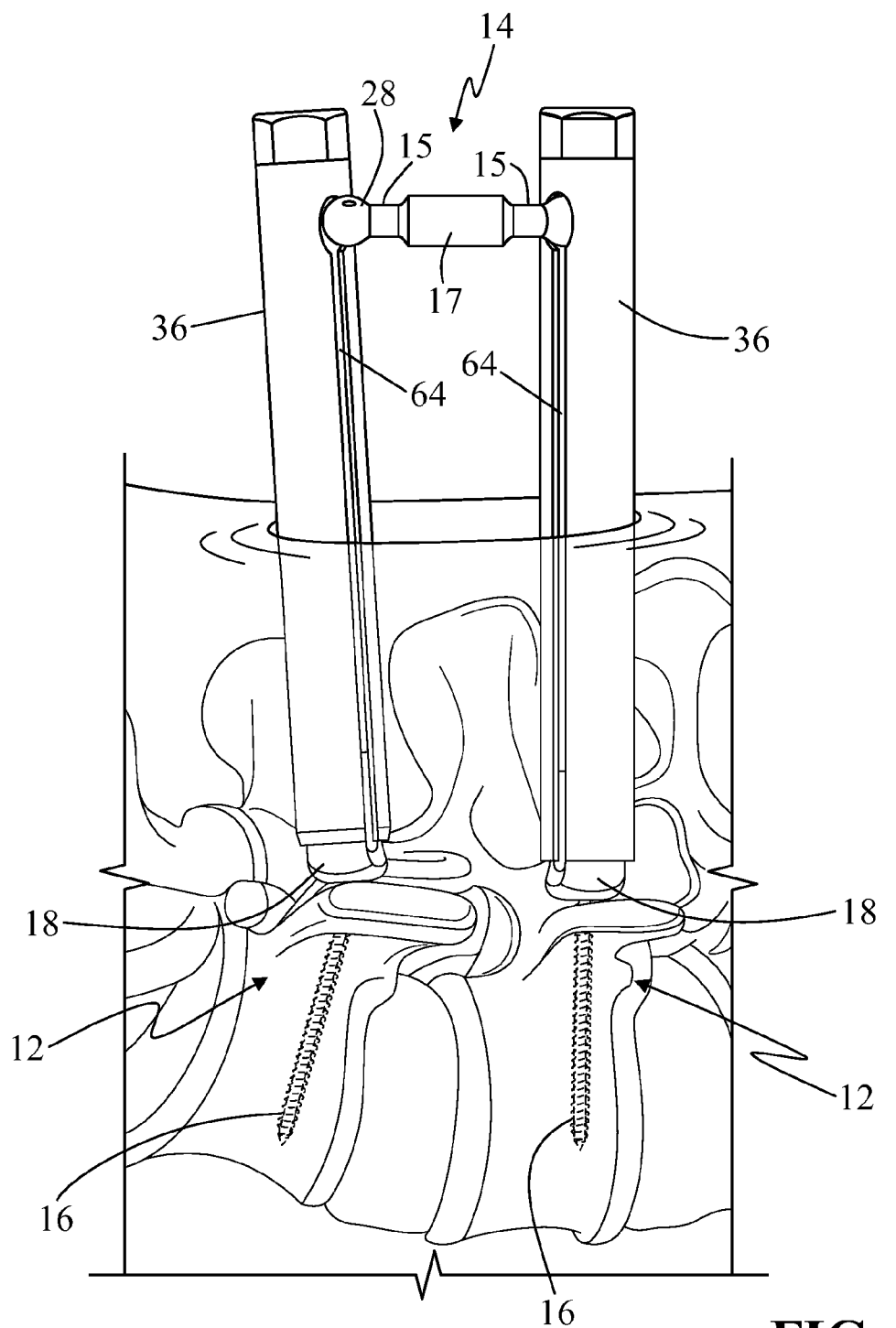
FIG. 23 illustrates the insertion of the shaped ends of the connecting element into the guide member keyhole during the minimally invasive insertion of the spinal fixation system of FIG. 1 according to an exemplary embodiment of the present invention.
Figure 24:
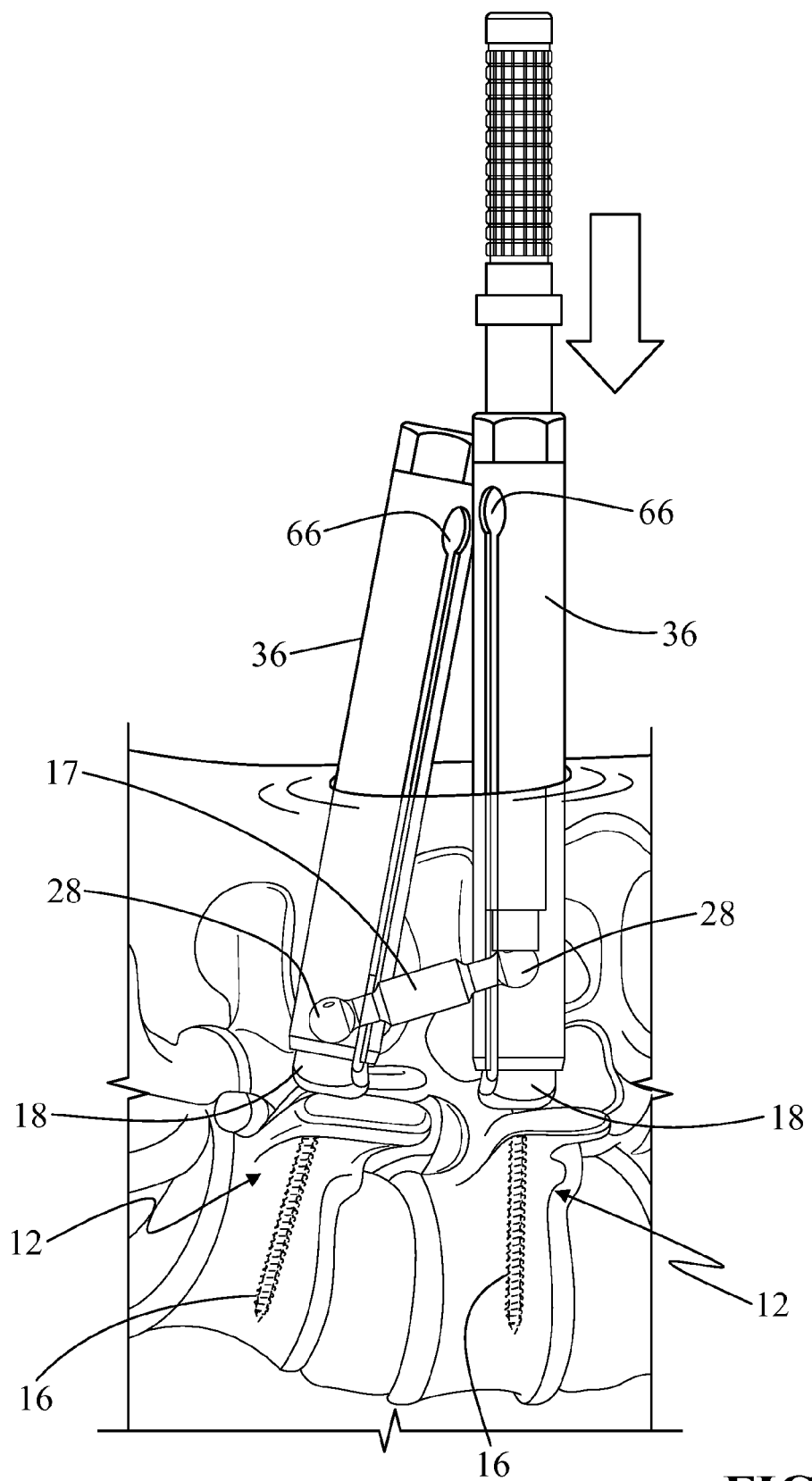
FIG. 24 illustrates the significant aspect of guiding of the connecting element into the pedicle screw during the minimally invasive insertion of the spinal fixation system of FIG. 1 according to an exemplary embodiment of the present invention.

With the inner sleeve members 38 removed from the guide members 36, the shaped ends 28 of the connecting element 14 may then be inserted into the keyhole 66 on each guide member 36, as seen in FIG. 23. At that point, as best viewed in FIG. 24, the connecting element 14 may be urged downwards within the guide channels 64 of the guide member 36, through the minimally disruptive incision created between the adjacent guide members 36 (between the patient's skin and the approximate pedicle target site), until the shaped ends 28 are positioned within the correspondingly shaped receiving areas within the pedicle screw housing 18. If necessary, a pushing instrument (not shown) may be used to push the connecting element 14 down the guide member 36.

Figure 25:
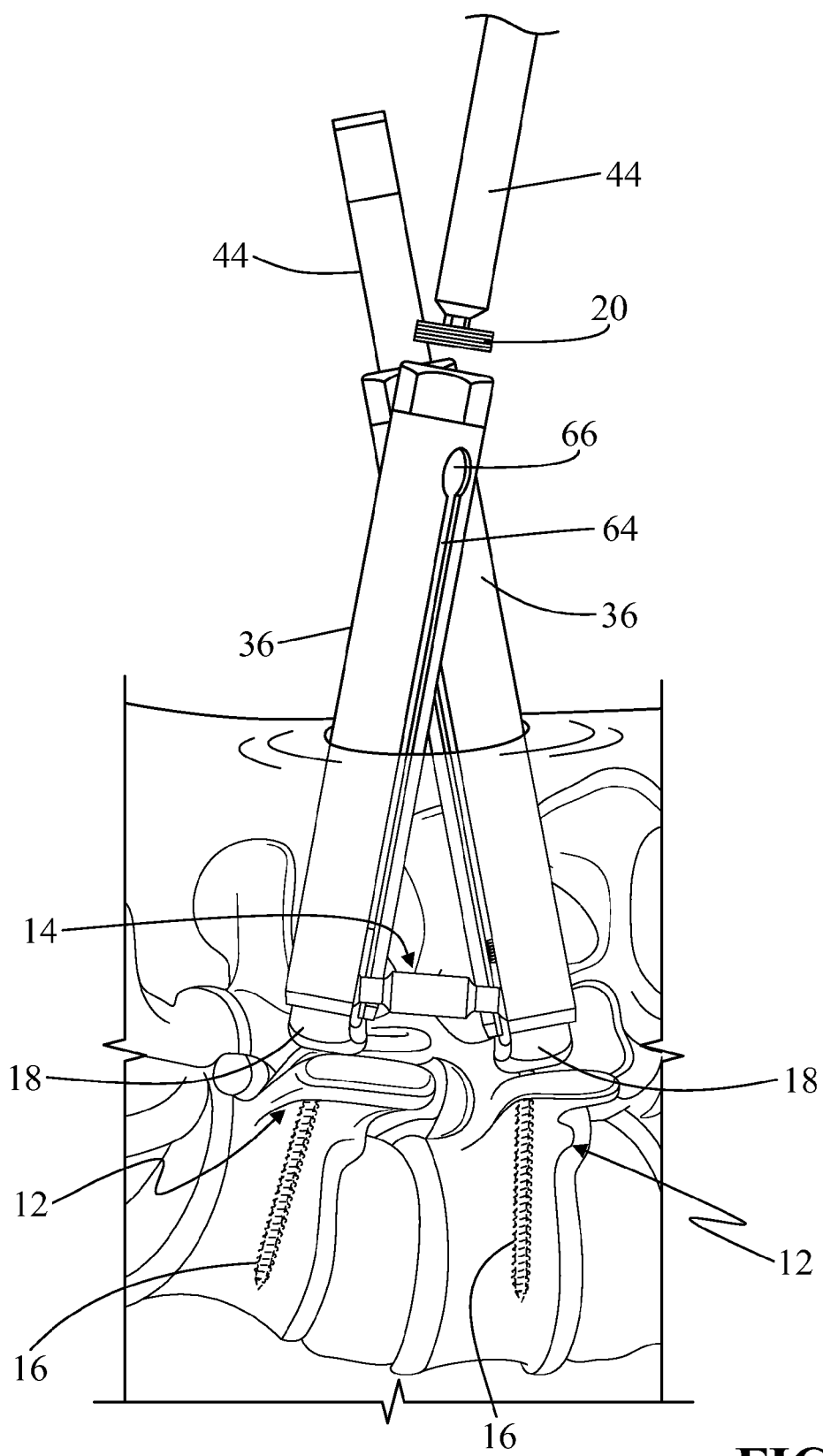
FIG. 25 illustrates the method of inserting lock screws for locking the connecting element in place within the pedicle screw during the minimally invasive insertion of the spinal fixation system of FIG. 1 according to an exemplary embodiment of the present invention.
Figure 26:
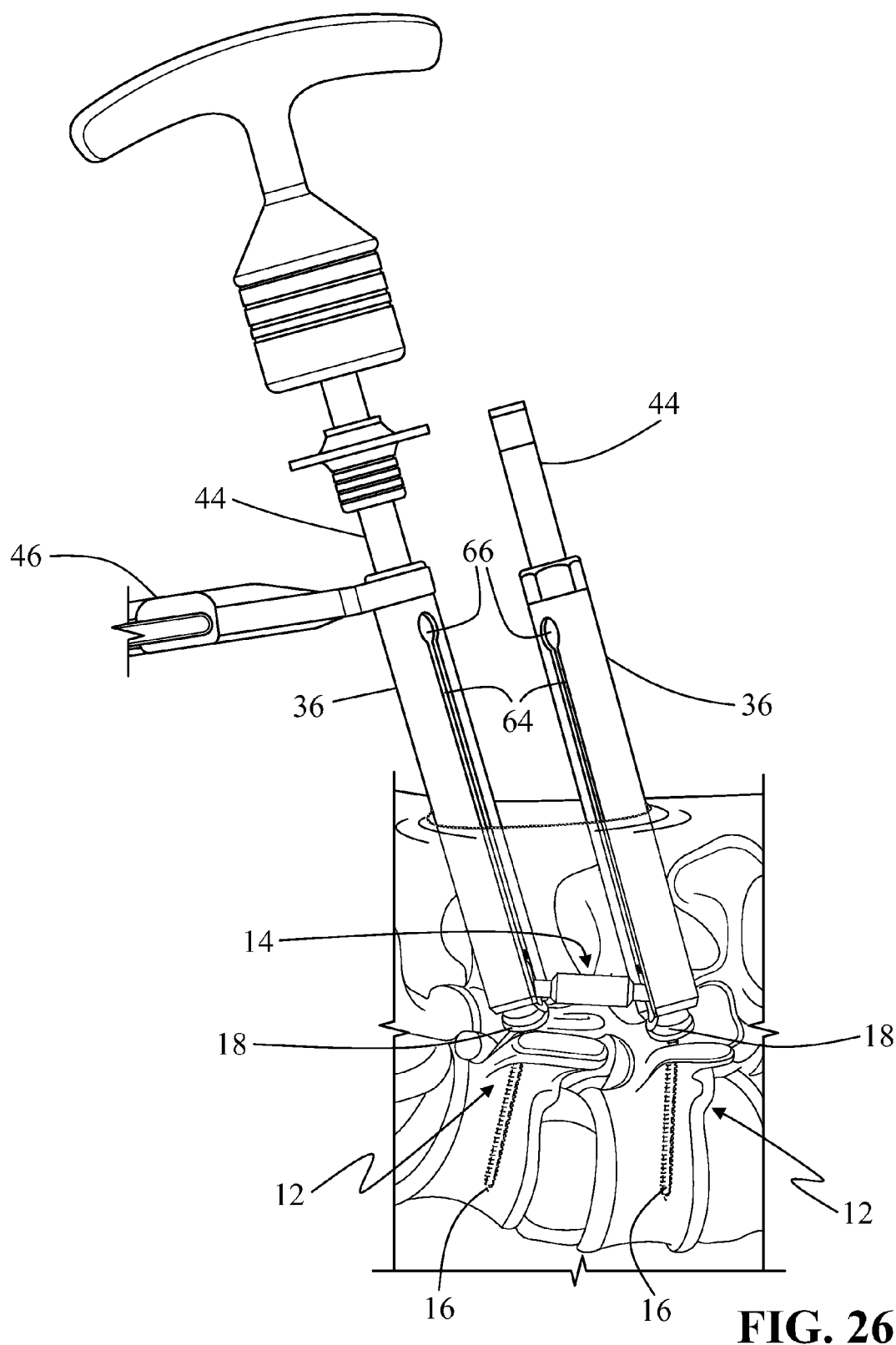
Figure 27:
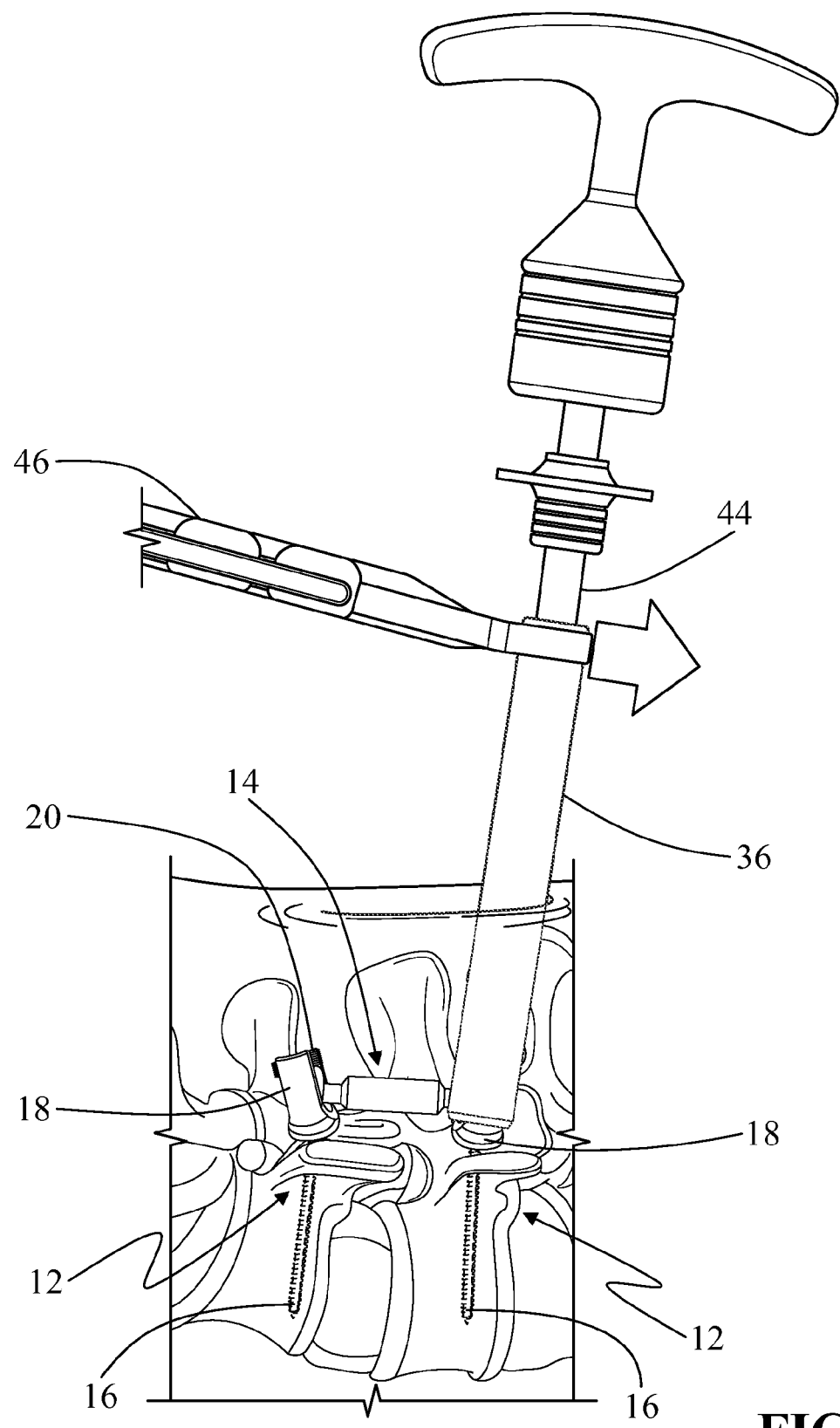

As shown in FIG. 25, the lock screws 20 of the spinal fixation system 10 may then be advanced through the guide member 36 and locked over the shaped ends 28 of the connecting element 14 via the lock screw driver 44. If distraction or compression is desired, the lock screws 20 may be tightened until snug and then backed off slightly. According to important aspects of the present invention, "instrument free" distraction may be achieved simply be deflecting the guide members 36 toward each other (as in FIG. 25) and retightening the lock screws 20, while "instrument free" compression may be accomplished by deflecting the guide members 36 away from each other (as in FIG. 26-27). The term "instrument free" is used herein to mean that the present invention can accomplish desired compression and/or distraction without the need for separate, dedicated compression and/or distraction instruments. This, it will be appreciated, is advantageous in that it saves valuable operative time by not causing the surgeon to switch instruments in order to perform compression and/or distraction, and also saves manufacturing costs via the elimination of the otherwise dedicated compression and/or distraction instruments. As shown in FIGS. 26-27, a counter torque wrench 46 may be applied to the proximal end of the guide member 36 to facilitate the final tightening of the lock screws 20.

Figure 28:
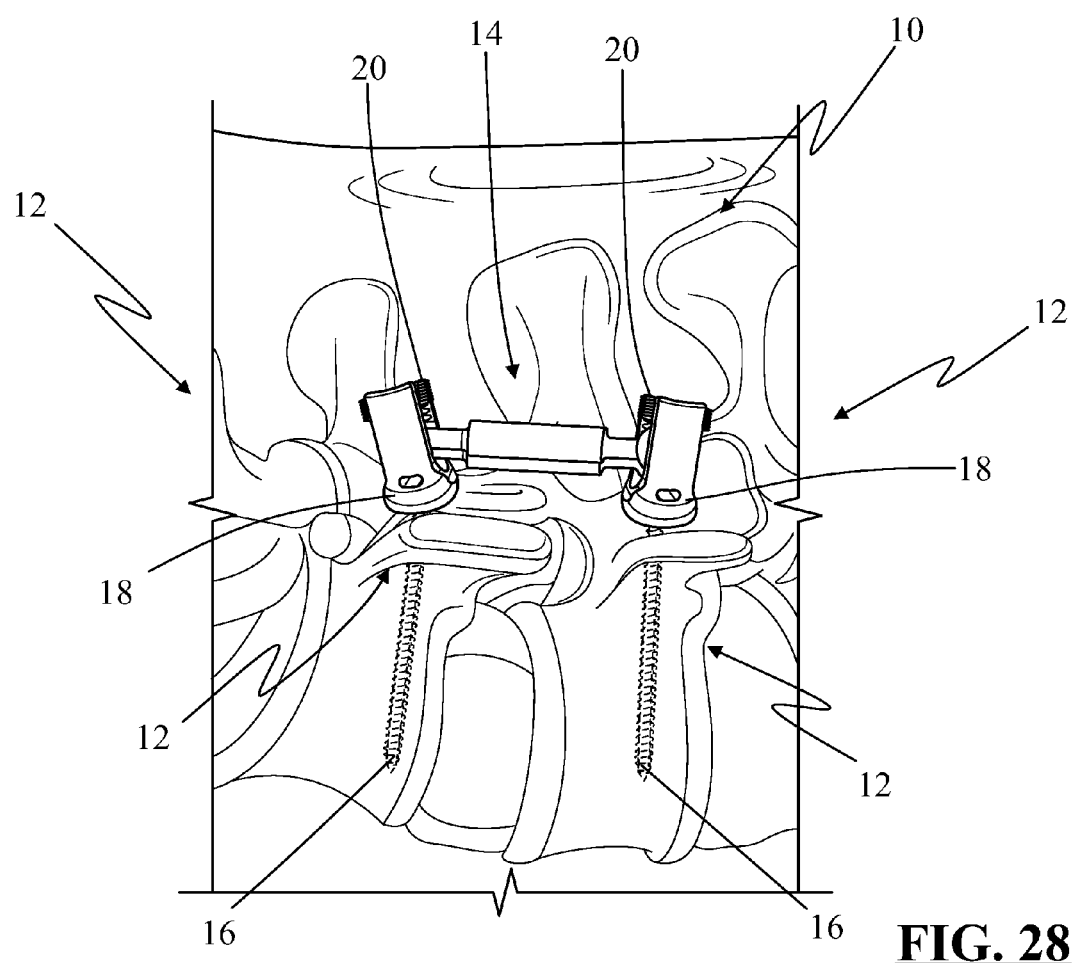
FIG. 28 illustrates the spinal fixation system of FIG. 1 after insertion using the minimally invasive insertion system of FIG. 5, according to an exemplary embodiment of the present invention.

With the final tightening of the lock screws 20 complete, the guide members 36 may then be removed, which results in the final implanted "single level" spinal fixation system 10 as shown in FIG. 28. If desired the procedure may be repeated on the contralateral side to achieve greater fixation. The procedure may also be carried out simultaneously on both sides if desired. In either event, the spinal fixation system 10 of the present invention, via the use of the introduction system 30 of the present invention, advantageously accomplishes minimally disruptive spinal fixation between adjacent vertebral bodies.

Figure 29:
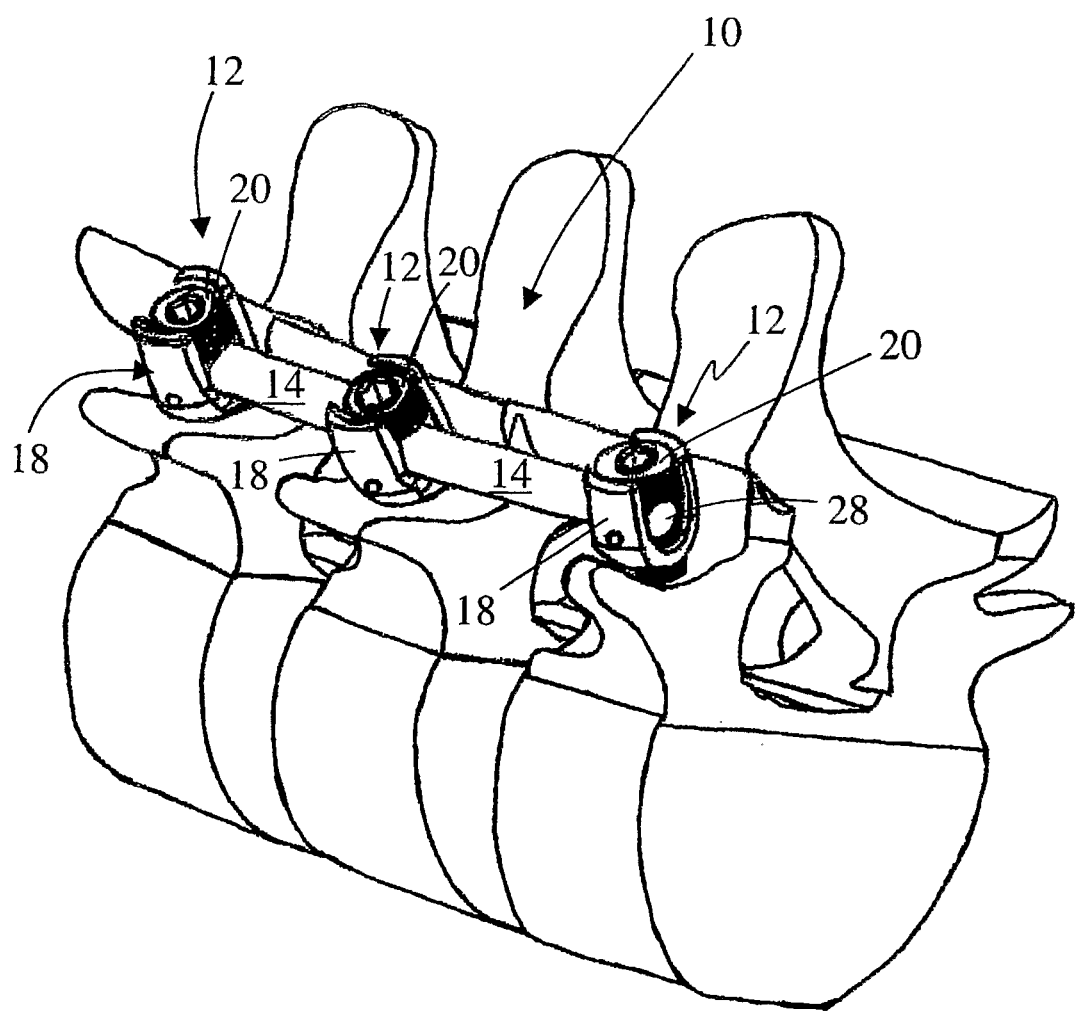
FIG. 29 is a perspective view of a "multi level" spinal fixation system in use according to the present invention, including (by way of example only) first, second and third pedicle screws and a connecting element having dual shaped portions on either end, according to an exemplary embodiment of the present invention
Figure 30:
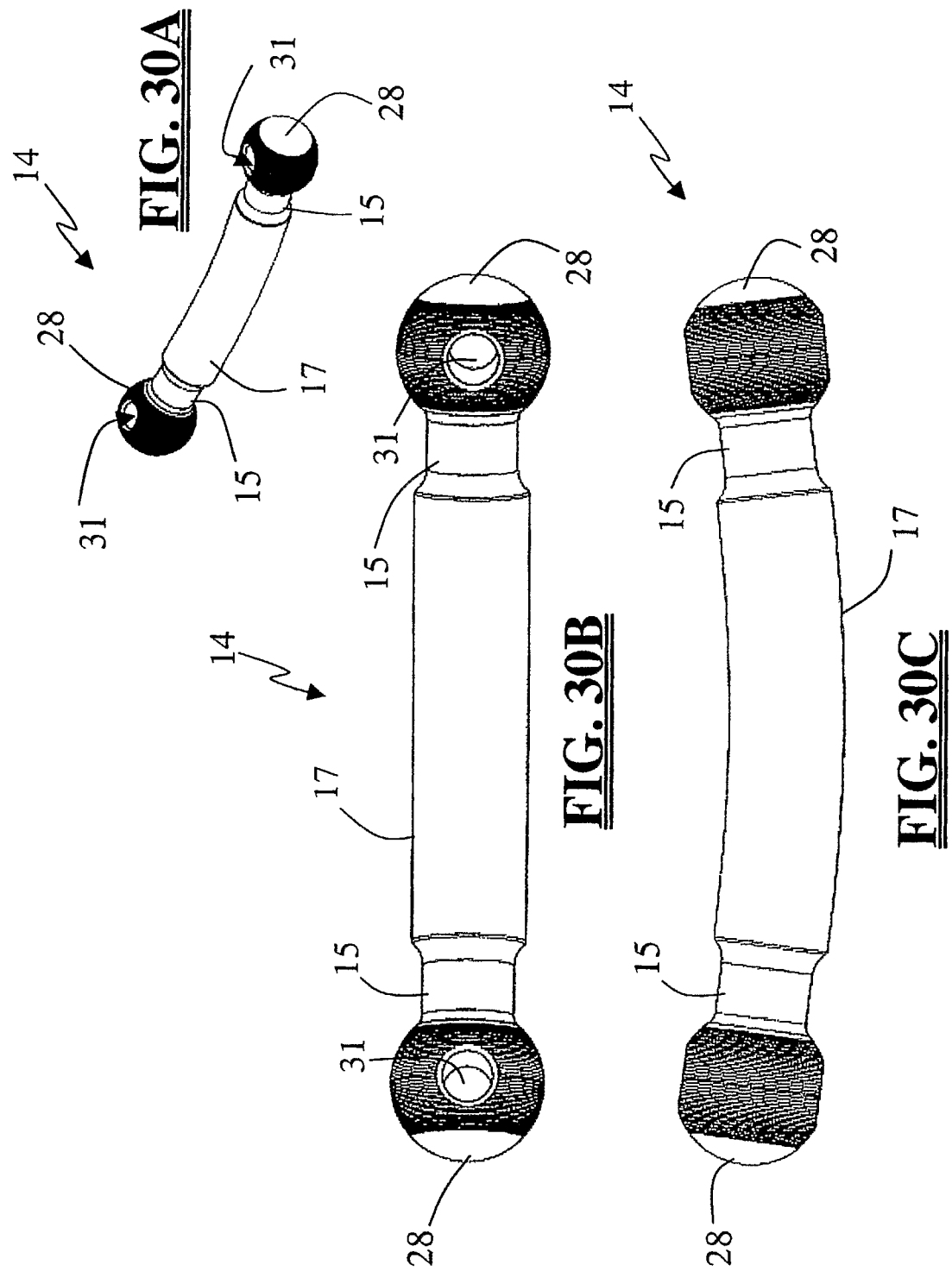
FIGS. 30A-30C illustrate an embodiment of an elongated connecting element having shaped ends for use in a "multi level" fixation, according to an exemplary embodiment of the present invention.
Figure 31:
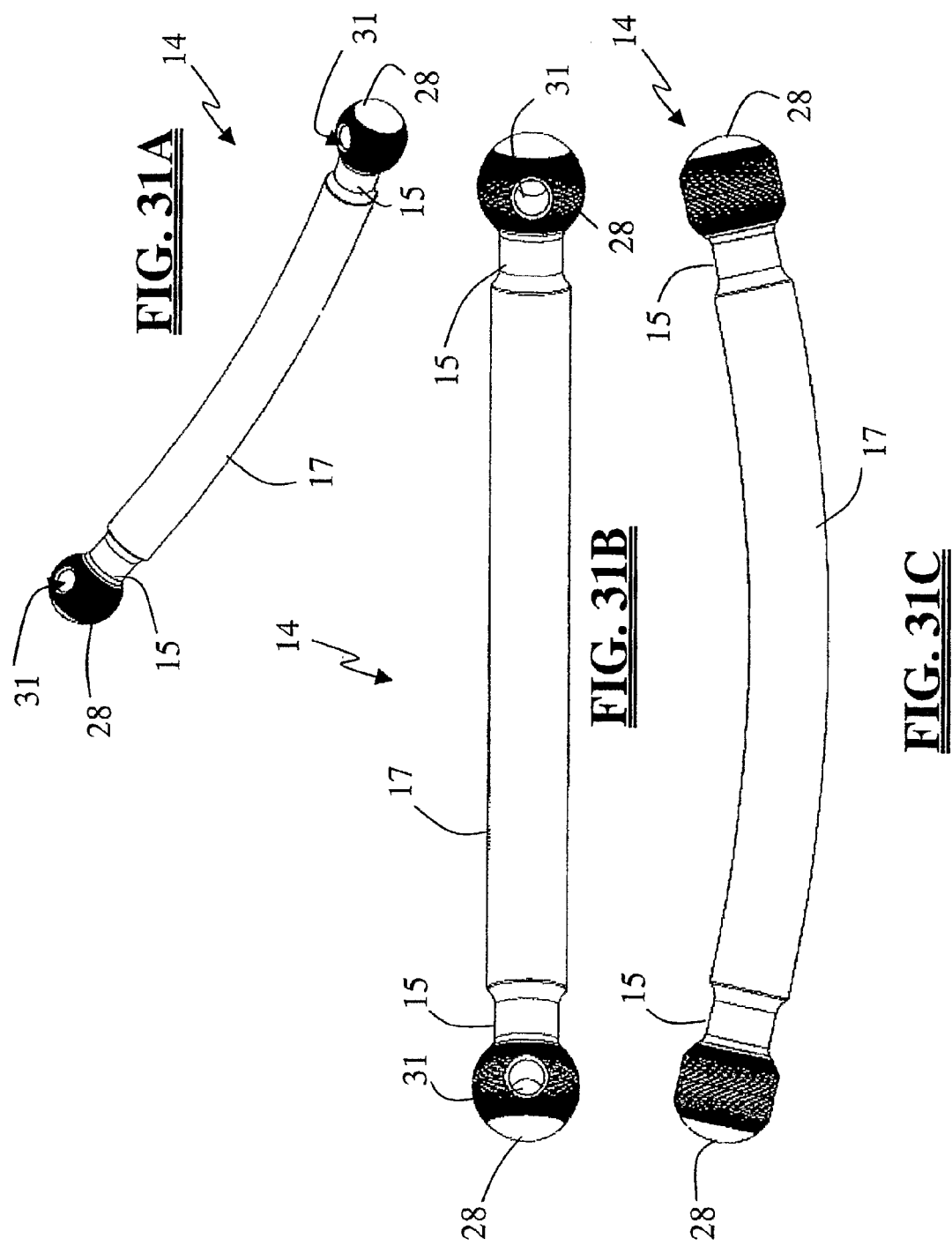
FIGS. 31A-31C illustrate another embodiment of an elongated connecting element having shaped ends for use in a "multi level" fixation, according to an exemplary embodiment of the present invention.

FIG. 29 illustrates the spinal fixation system 10 according to the "multi-level" embodiment of the present invention, meaning it spans at least three vertebrae (e.g. two vertebral levels). The spinal fixation system 10 accomplishes this, by way of example only, via the use of at least three pedicle screw assemblies 12 implanted in adjacent pedicles along the spine and by providing the connecting element 14 having length and configuration sufficient to be coupled to each pedicle screw assembly 12. Although not shown, it is to be appreciated as within the scope of the present invention to accomplish this by omitting one or more of the "middle" pedicle screw assemblies 12 such that the connecting element 14 simply spans at least three pedicles while only being affixed to the superior and inferior pedicles. In either event, the pedicle screw assemblies 12 employed in the multi-level embodiment are identical in construction as shown and described above with reference to the single level embodiment, such that a repeat discussion of the common elements is unnecessary.

FIGS. 30A-30C and 31A-31C illustrate various connecting elements 14 for use in the "multi-level" embodiment of the present invention. The main distinction from the "single level" embodiment is that the connecting elements 14 are preferably slightly curved in nature so as to better accommodate the natural curvature of the spine over multiple vertebral levels. The "multi-level" connecting elements 14 may be provided having any of a range of suitable dimensions to accommodate the anatomical and pathologic considerations of the given patient for multi-level applications, including but not limited to a length (including the shaped ends 28) ranging from 25 mm to 70 mm. Although shown as generally curved, it will be appreciated that the connecting elements 14 in the multi-level embodiment may be provided as generally straight if desired. Other than these distinctions, the connecting elements 14 of the multi-level embodiment are identical in construction to those shown and described above with reference to the single level embodiment, such that a repeat discussion of the common elements is unnecessary.

The shaped ends 28 on the connecting element 14 provide the same advantages described with reference to the single level embodiment, namely it avoids the "overhang" prevalent with prior art pedicle systems which employ straight rods as connecting elements (without shaped ends), and provides the ability to rotate the housing of the poly-axial pedicle screw assemblies 12 about the shaped end 28 to accomplish "instrument free" compression and/or distraction via the use of the guide members 36 of the minimally disruptive introduction system 30 of the present invention.

Figure 32:
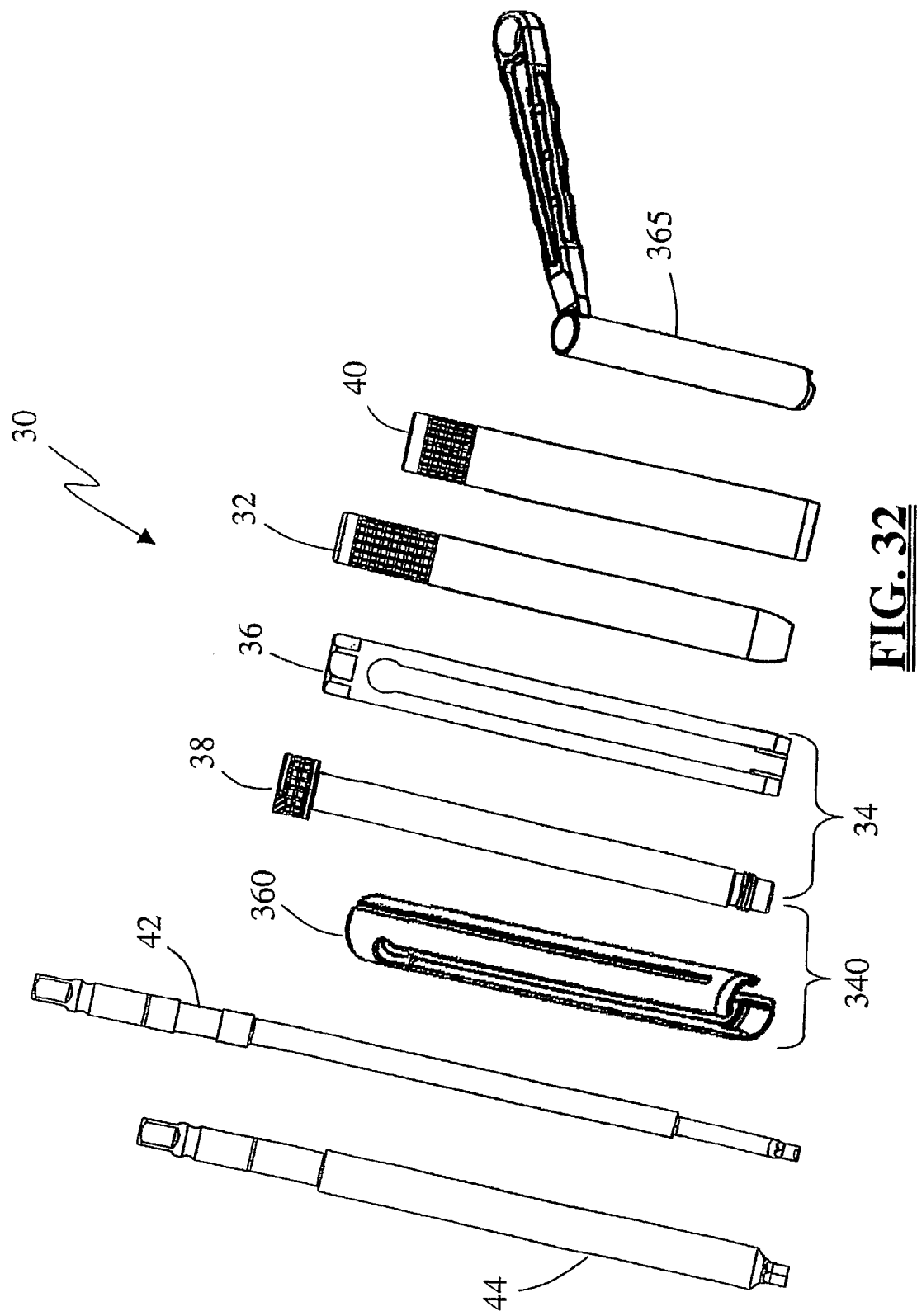
FIG. 32 illustrates a system for surgically introducing the "multi level" spinal fixation system of FIG. 29 in a minimally invasive fashion, including (By way of example) a tap insulator, guide assembly (comprising a guide member and an inner sleeve), guide assembly insulator, pedicle screw driver, and a lock screw driver, split guide member, and a counter torque tube, according to an exemplary embodiment of the present invention.

FIG. 32 illustrates the minimally disruptive introduction system 30 for introducing the spinal fixation system 10 according to the "multi-level" embodiment of the present invention. The main distinction between the "single level" embodiment is that the introduction system 30 includes a spilt guide member 360 and a counter torque tube 365 in addition to the instruments shown and described above with reference to the "single level" embodiment. When coupled together with the inner sleeve 38 (as will be described below), the split guide member 360 comprises a center guide assembly 340. Other than these distinctions (which will be detailed below), the introduction system 30 of the multi-level embodiment is identical in construction to that shown and described above with reference to the single level embodiment, such that a repeat discussion of the common elements is unnecessary.

FIGS. 33A-33C illustrate in detail various aspects of the split guide member 360 according to an exemplary embodiment of the present invention. Split guide member 360 has a generally elongated cylindrical shape with a length sufficient to extend from a pedicle target site at a distal end 560, to a position outside the surgical corridor at a proximal end 580, as best viewed in FIG. 39. An interior lumen 600 extends from distal end 560 to proximal end 580. The split guide member 360 includes a guide channel 640 having an enlarged keyhole opening 660 at a proximal end and an open distal end.

In a significant aspect of the present invention, two guide channels 640 are located on split guide member 360 approximately 180 degrees from one another. Guide channels 640 pass into the interior lumen 600 and extend substantially along the split guide member 360 from distal end 560 to a position short of proximal end 580. The proximal ends of guide channels 640 comprise keyholes 660 dimensioned to receive the shaped end 28 of the multi-level connecting element 14. More specifically, the shaped end 28 on one end of the connecting element 14 is preferably passed though the keyhole 660 on one side of the split guide member 360 and then through the keyhole 660 on the other side of the split guide member 360 such that the central section 17 of the connecting element 14 may thereafter be passed downward through the guide channel 640. The downward progression of the connecting element 14 may progress until the central section 17 is disposed within the housing 18 of the middle pedicle screw assembly 12 and the shaped ends 28 are disposed within the housing 18 of the superior and inferior pedicle screw assemblies 12. In addition to the guide channels 640, the split guide 360 also includes two longitudinal grooves 645 positioned approximately ninety (90) degrees from the guide channels 640 and extending from the proximal end 580 to a point short of the distal end distal end 560. As will be discussed below, grooves 645 mate with interior ridges 395 provided on the counter torque tube 365.

Split guide member 360 preferably comprises a surgical grade metal such as, by way of example, stainless steel, aluminum and/or titanium, although other biologically suitable compositions (such as, by way of example, plastics, ceramics, and/or carbon composites) may be employed as well. The split guide member 360 may be provided having any number of suitable dimensions to accommodate the anatomical and pathologic considerations of the given patient, including but not limited to a length ranging from 4 to 6 inches.

Figure 40:
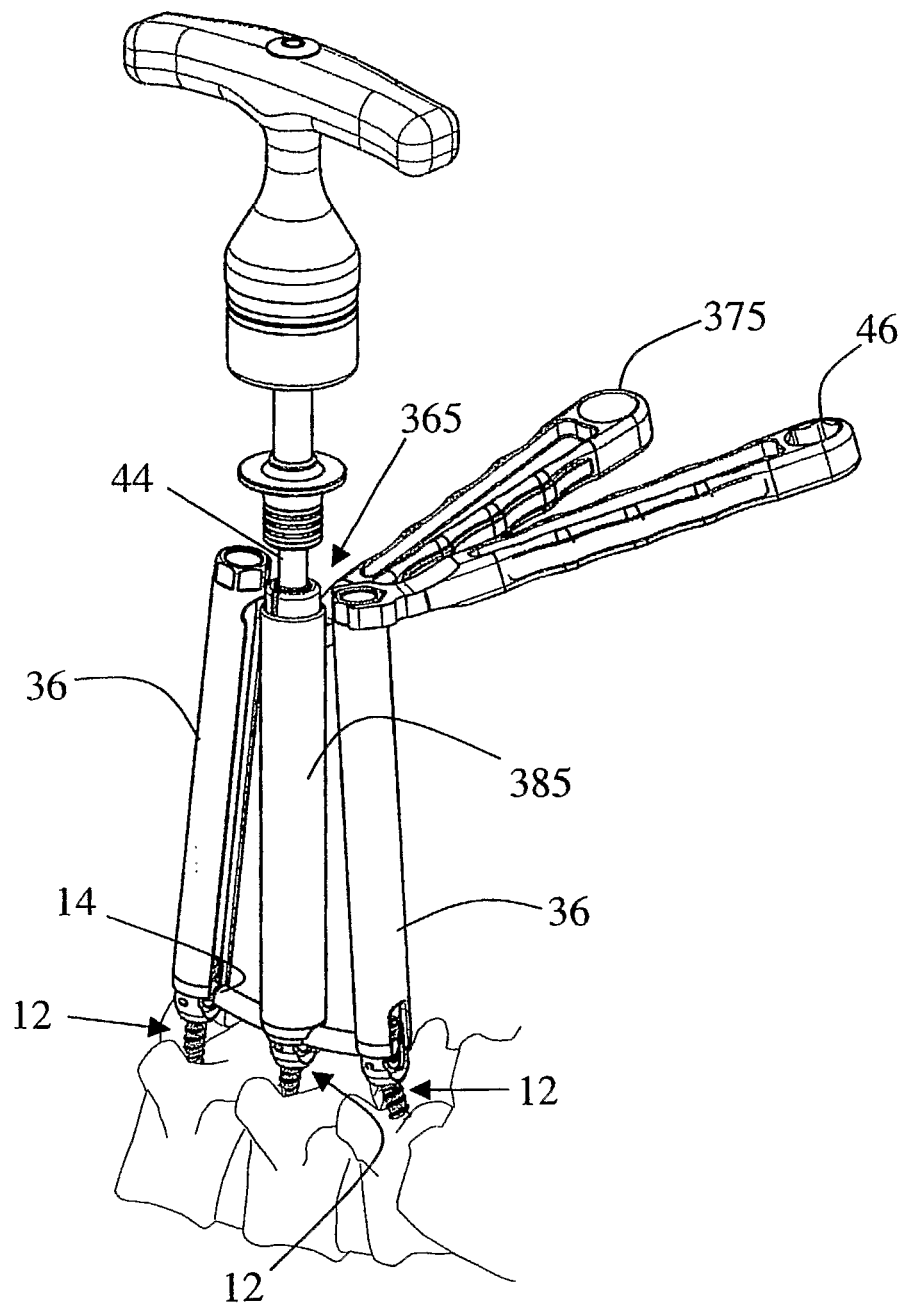
FIG. 40 illustrates the use of the counter torque tube during insertion of the center lock screw during a "multi level" spinal fixation, according to an exemplary embodiment of the present invention.
Figure 41:
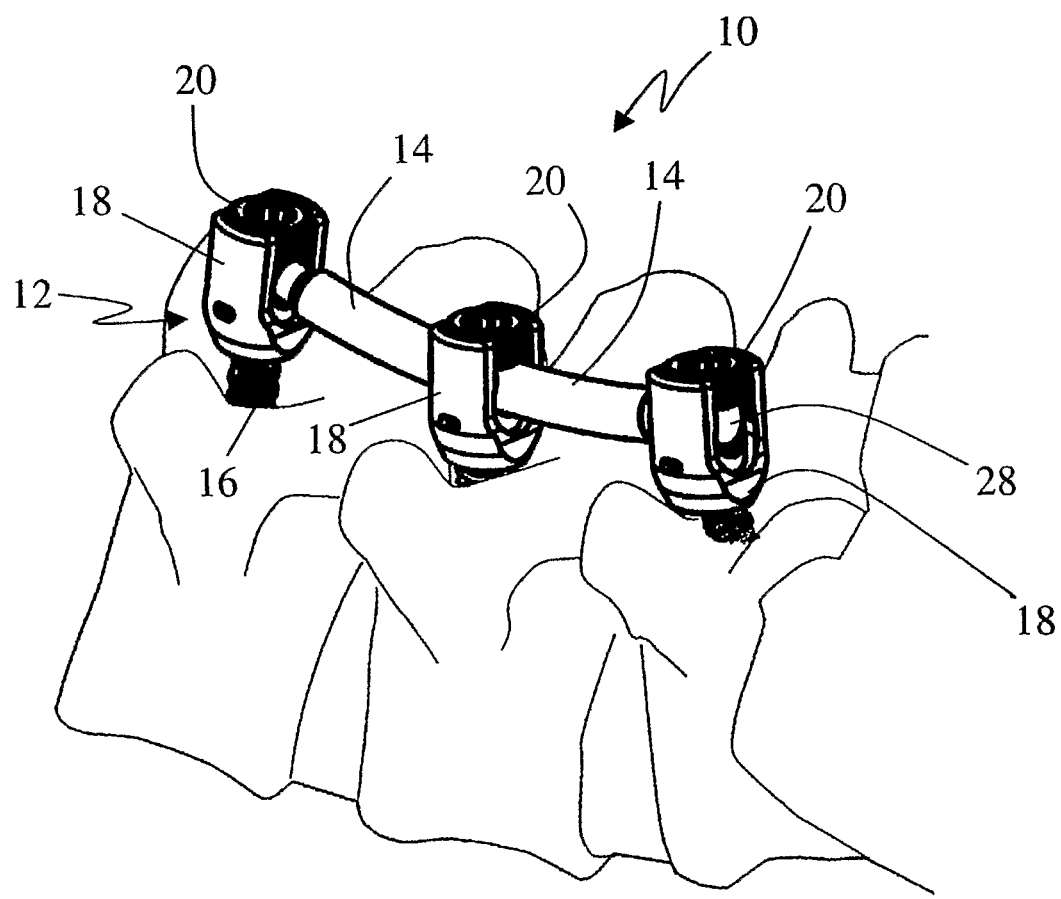
FIG. 41 illustrates the spinal fixation system of FIG. 1 after insertion using the minimally invasive insertion system of FIG. 5, according to an exemplary embodiment of the present invention.

FIGS. 34A-34C illustrate in detail the center torque tube 365 of the system 30 according to an exemplary embodiment of the present invention. Counter torque tube 365 comprises a handle 375 and a generally elongate tube 385. The handle 375 may be fixedly or detachably coupled to the elongate tube 385. Tube 385 has a generally elongated cylinder shape with a length matching approximately that of the spilt guide member 360, as shown in FIG. 40. As best shown in FIG. 34B, the tube 385 includes a lumen 387 extending between a distal end to a proximal end with one or more ridges 395 disposed along the interior of the lumen 387. The ridges 395 are preferably disposed generally parallel to the central longitudinal axis of the tube 385. The ridges 395 may be provided with any suitable length, such as the approximate length of the grooves 645 of the split guide member 360 or any length short of that so long as it's sufficient to adequately engage the grooves 645 to prevent the unwanted rotation of the split guide member 360 when tightening the lock screws 20. The distal end of the tube 385 may also be equipped with a pair of recesses 389 located approximately ninety (90) degrees from one another and dimensioned to accommodate the central portion 17 of the connecting element 14 as shown in FIG. 40.

Tube 385 preferably comprises a surgical grade metal such as, by way of example, stainless steel, aluminum and/or titanium, although other biologically suitable compositions (such as, by way of example, plastics, ceramics, and/or carbon composites) may be employed as well. The tube 385 may be provided having any number of suitable dimensions to accommodate the anatomical and pathologic considerations of the given patient, including but not limited to a length ranging from 4 to 6 inches. The handle 375 may be any number of suitable lengths and dimensions to provide the surgeon with a sufficient purchase on the tube 385 during use.

The spinal fixation system 10 and minimally disruptive introduction system 30 of the "multi-level" embodiment of the present invention system may be employed as follows (with common steps from the "single level" embodiment selectively omitted as unnecessary). Pedicle target sites are accessed and pilot holes are formed and tapped according to the procedure described above with reference to FIGS. 13-15. Coupling the pedicle screw assemblies 12 to the guide assemblies 34 may then be carried out as described above with reference to FIGS. 16-18. Given the "multi-level" embodiment, an additional pedicle screw assembly 12 may be coupled to a center guide assembly 340 (FIG. 32) by substituting the guide member 36 for the split guide member 360 in the process described above with reference to FIGS. 16-18. Once the superior and inferior pedicle screw assemblies 12 are coupled to respective guide members 34, and the middle pedicle screw assembly 12 is coupled to the center guide assembly 340, then screw placement may commence according to the present invention.

Figure 35:
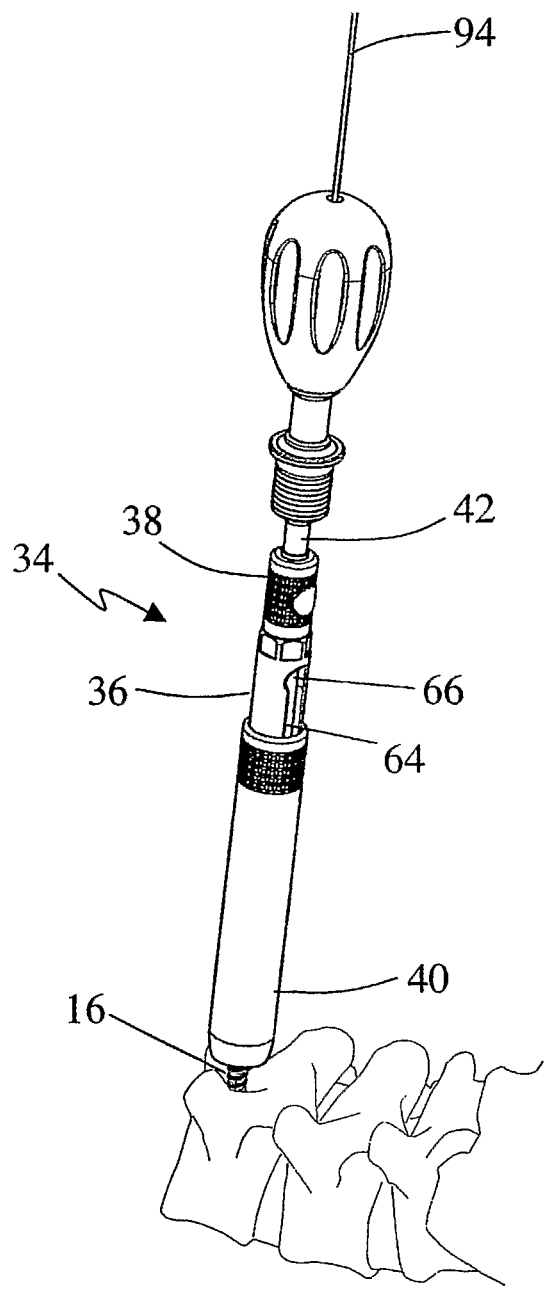
FIG. 35 illustrates a guide assembly in use during minimally invasive pedicle screw insertion according to an exemplary embodiment of the present invention.
Figure 36:
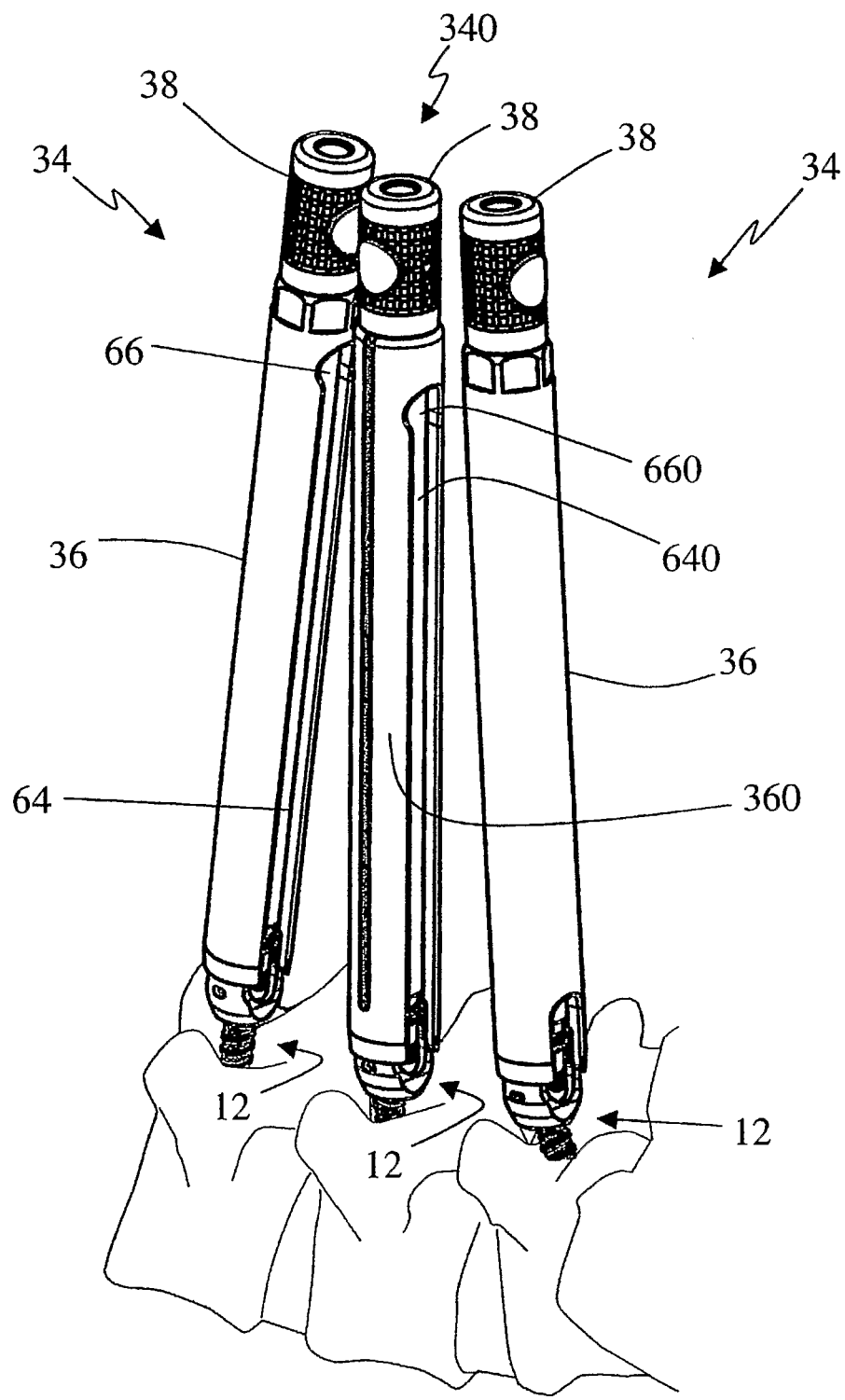
FIG. 36 illustrates two guide assemblies and a center guide assembly during use during a "multi level" spinal fixation, according to an exemplary embodiment of the present invention.

Prior to discussing the process of "multi-level" screw placement, it is to be appreciated that, although the skin and tissue of the patient is not shown in FIGS. 35-41, the spinal fixation system 10 and introduction system 30 of the "multi-level" embodiment may be introduced in the same minimally disruptive manner with the same benefits described in detail above. As shown in FIG. 35, the guide insulator 40 and guide assembly 34 are introduced into one of the superior or inferior pedicle target sites, as described above with reference to FIG. 19. As shown in FIG. 36, the center guide assembly 340 should then be positioned over a centrally located vertebra (such as the middle vertebra shown in the two level example shown by way of example) and the central pedicle screw assembly 12 introduced in the same manner as the superior and inferior pedicle screw assemblies 12 as described above with reference to FIGS. 19-20. When all the screws 12 are in place the screw driver 42 and guide insulators 40 are removed leaving the guide assemblies 34 and center guide assembly 340 in place, as viewed in FIG. 36.

Figure 37:
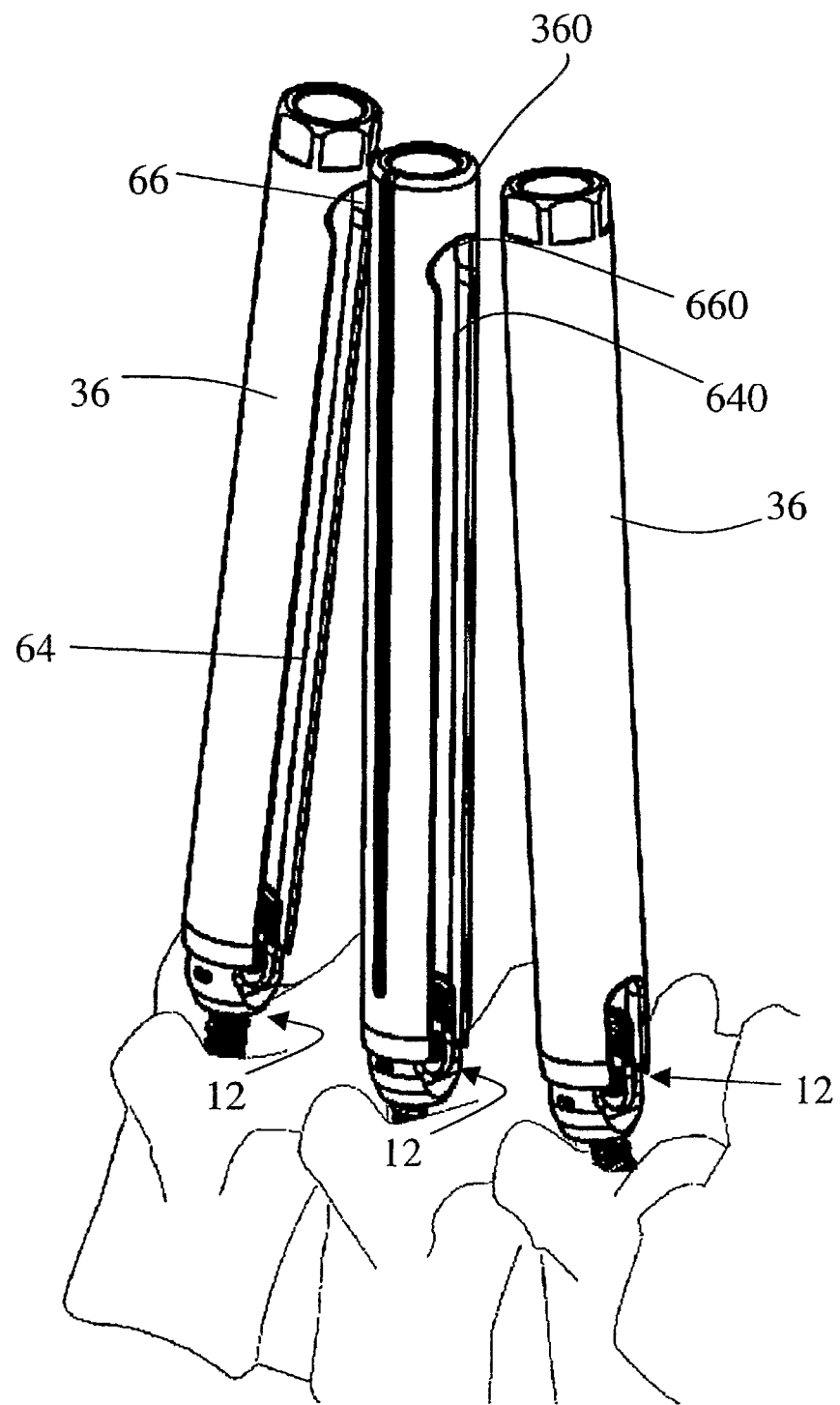
FIG. 37 illustrates two guide members and a split guide member after removal of sleeve members during a "multi level" spinal fixation, according to an exemplary embodiment of the present invention.
Figure 38:
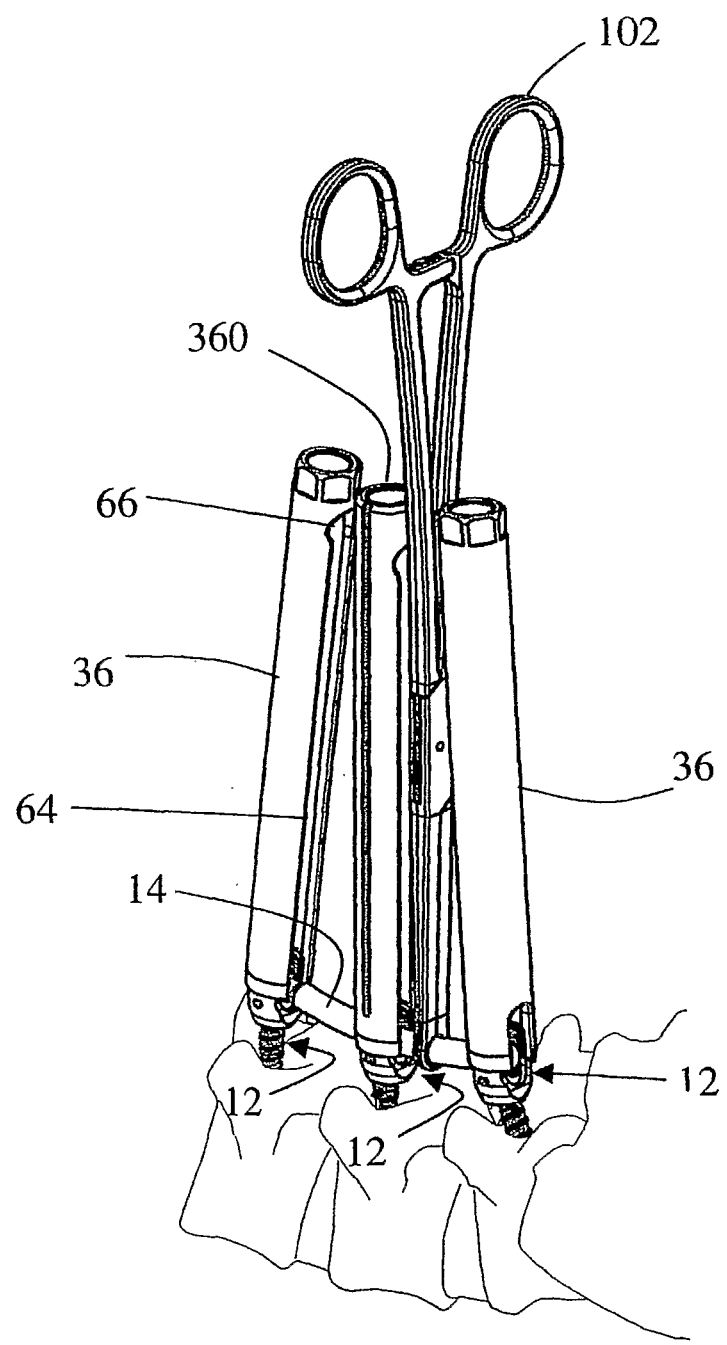
FIG. 38 illustrates insertion of the connecting element through the split guide and guide members during a "multi level" spinal fixation, according to an exemplary embodiment of the present invention.

An appropriately sized connecting element 14 may be selected based on the experience and particular needs of the surgeon and patient anatomy, including but not limited to the manner described above with reference to FIG. 21 (using the guide assemblies 34). At this point, the inner sleeve members 38 may be unthreaded and removed from the guide assemblies 34 and 340, as shown in FIG. 37, taking care not to dislodge the guide members 36 and/or split guide member 360 from screw housings 18. The connecting element 14 may then be inserted through the split guide member 360 utilizing the keyholes 660 as described above with reference to FIGS. 33A-33C. The shaped ends 28 are then inserted into the superior and inferior guide members 36 by way of keyholes 66 as described above with reference to FIG. 23. The connecting element 14 may then be advanced downwards into the guide channels 64 and 640 of the respective guide members 36, 360 such that the shaped ends 28 are disposed within the superior and inferior pedicle screw housings 18 as described above with reference to FIG. 24 and the central portion 17 is disposed within the central pedicle screw housing 18 as shown in FIG. 38. If necessary, a rod pusher or rod clamp 102 may be used to push connecting element 14 down the guide members 36 and split guide member 360, as pictured in FIG. 38.

Figure 39:
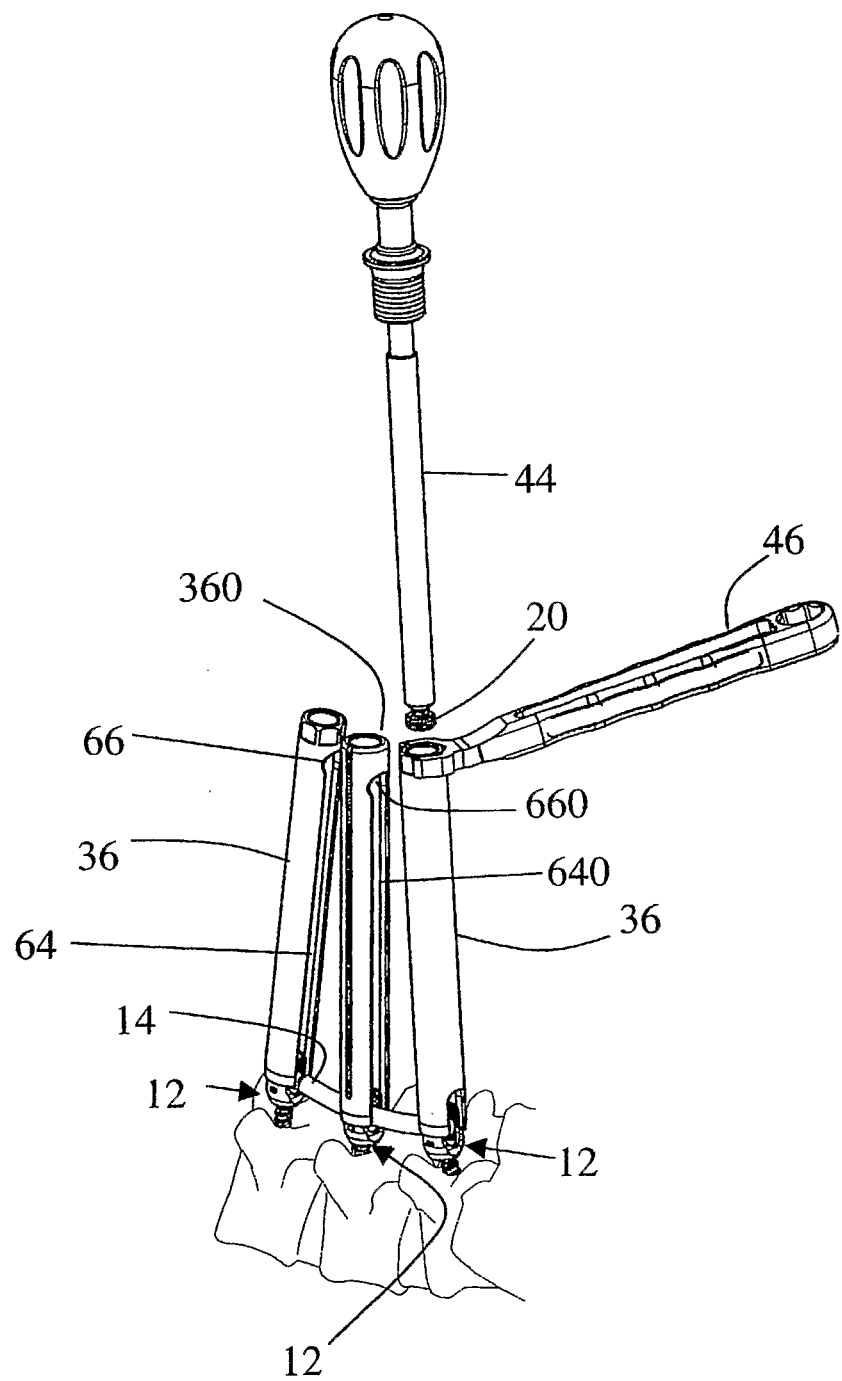
FIG. 39 illustrates the use of a counter torque wrench for insertion of a lock screw during a "multi level" spinal fixation, according to an exemplary embodiment of the present invention.

FIG. 39 illustrates the step of inserting lock screws 20 through the guide members 36 and split guide 360 using the lock screw driver 44. If distraction or compression is desired, the lock screws 20 may be tightened until snug and then backed off slightly. Distraction may be achieved in a preferred method by tightening the center lock screw 20 as shown in FIG. 40 and deflecting the guide members 36 toward each other as described above with reference to FIG. 25. Compression may be achieved in a preferred method by tightening the center lock screw 20 as shown in FIG. 40 and deflecting the guide members 36 away from each other as described above with reference to FIGS. 26-27.

As shown in FIG. 40, the central lock screws 20 are preferably tightened by utilizing the counter torque tube 365. The counter torque tube 365 is inserted over the split guide member 360 such that its interior ridges 395 mate with the grooves 645 of guide 360, thereby preventing rotational movement as torque is applied to the lock screws 20 until a final locked position is achieved. A counter torque wrench 46 may be applied to the superior and/or inferior guide members 36 to facilitate the final tightening of the superior and/or inferior lock screws 20. As pictured in FIG. 41, after final tightening of the lock screws 20, the guide member 36 and split guide member 360 are removed and multilevel fixation is complete. If desired the procedure may be repeated on the contralateral side to achieve greater fixation. Alternatively, the procedure may be carried out simultaneously on both sides.

While the invention is susceptible to various modifications and alternative forms, specific embodiments thereof have been shown by way of example in the drawings and are herein described in detail. For example, although described primarily for use in tissue sparing, minimally disruptive surgery, it will be appreciated that the spinal fixation system 10 and introduction system 30 may also be used in a traditional "open" procedure as well, wherein the surgical incisions are large and with a high degree of tissue and muscle disruption relative to the minimally disruptive procedure described herein. It is also within the scope of the invention to introduce dynamic pedicle-based fixation systems in the same manner described herein, provided the dynamic stabilization system is equipped with a coupling element (flexible and/or rigid) having shaped ends as described herein. The description herein of specific embodiments is not intended to limit the invention to the particular forms disclosed, but on the contrary, the invention is to cover all modifications, equivalents, and alternatives falling within the spirit and scope of the invention.

What is claimed is:

1. A spinal fixation system for fixing target vertebrae of a spine, comprising:
   an elongate connecting element having first and second at least partially spherical shaped ends;
   first and second bone engaging fasteners each having a screw with a head and a housing adjustably coupled to said screw head at a screw coupled end such that the screw coupled end rotates about the screw head to adjust the angular orientation of the housing relative to the screw, and wherein said housings each have a cavity situated above the screw coupled end, the cavity configured to wholly receive either of said first shaped end and said second shaped end therein and such that the housing is rotatable about the first or second shaped end received therein which repositions the screw coupled end and coupled screw relative to the shaped end received therein; and
   first and second guide members that are mateable with said housings of the first and second bone engaging fasteners at a guide coupled end opposite the screw coupled end and that are configured to guide said elongate connecting element into said first and second bone engaging fastener housings, wherein angulating at least one of the first and second guide members to adjust the angular orientation of the mated housing causes said housing to rotate about said shaped end received therein repositioning the screw coupled end and coupled screw relative to the shaped end to thereby effect one of spinal compression and spinal distraction between said target vertebrae.

2. The system of claim 1, wherein said elongate connecting element spans between two target vertebrae.

3. The system of claim 1, wherein said elongate connecting element spans at least three target vertebrae.

4. The system of claim 3, including a third bone engaging fastener disposed between said first and second bone engaging fasteners.

5. The system of claim 4, comprising a third guide member having two enlarged openings dimensioned to receive said shaped ends of said connecting element and an elongate slot extending from each said enlarged opening to the distal end of said third guide member, said slots formed on opposite sides of said third guide member to allow the shaped ends of said connecting element to pass through said enlarged opening and a central portion of said connecting element to be disposed within said elongated slots.

6. The system of claim 5, wherein said third guide member is retained during use by a retaining element.

7. The system of claim 6, wherein said retaining element is generally tubular and encompasses at least a portion of said third guide member during use.

8. The system of claim 3, wherein said first and second bone engaging fasteners are coupled to one of adjacent target vertebrae and non-adjacent target vertebrae.

9. The system of claim 1, wherein at least one of said shaped ends is cannulated.

10. The system of claim 1, wherein said elongate connecting element is straight.

11. The system of claim 1, wherein each of said housings is equipped with a locking mechanism for locking said shaped ends of said connecting element within said respective housings.

12. The system of claim 11, wherein said locking mechanism comprises a threaded set screw for threaded engagement with threads formed within said respective housing.

13. The system of claim 1, wherein each guide member defines a lumen therethrough from a distal end to a proximal end, each guide member having at least one enlarged opening dimensioned to receive one of said shaped ends and an elongate slot extending from the enlarged opening to said distal end such that each shaped end is maintained within said lumen as said connecting element is advanced toward said bone engaging fasteners.

14. The system of claim 13, wherein the first and second guide members each have a length configured to extend at least between a respective housing and a body entry point when said first and second guide members are mated with said housings of said first and second bone engaging fasteners and said first and second bone engaging fasteners are anchored to a spine.

15. The system of claim 14, wherein the elongate slot on each guide member has a length configured such that the enlarged opening is situated externally to the body entry site when said first and second guide members are mated with said first and second bone engaging fasteners and said first and second bone engaging fasteners are anchored to a spine.

16. The system of claim 1, wherein said guide members are configured such that they may be manipulated to introduce said bone engaging fasteners into said target vertebrae.

17. The system of claim 16, wherein each guide member defines a lumen therethrough from a distal end to a proximal end, said lumen dimensioned to receive a sleeve member therethrough, said sleeve member comprising a distal end configured to releasably engage said housing.

18. The system of claim 17, wherein said sleeve member is configured to releasably engage said guide member.

19. The system of claim 1, wherein said elongate connecting element is curved.

20. A spinal fixation system, comprising:
   an elongate connecting element having first and second shaped ends;
   first and second bone engaging fasteners each having a screw and a housing for receiving respective shaped ends therein; and
   first and second guide members that are mateable with said first and second bone engaging fasteners and have a length to extend at least between a respective housing and a body entry point when said first and second guide members are mated with said first and second bone engaging fasteners and said first and second bone engaging fasteners are anchored to a spine, wherein each guide member defines a lumen therethrough from a distal end to a proximal end, each guide member having at least one elongate slot opening into said lumen and extending a majority of the length of the guide member from the distal end to a position short of the proximal end, wherein a proximal end of said at least one elongate slot connects with an enlarged opening having a width greater than a width of the elongate slot, wherein said shaped ends of said elongate connecting element are sized to fit through said enlarged opening but not said elongate slot such that said shaped end is maintained within said lumen as said connecting element is advanced toward said bone engaging fasteners.

21. The system of claim 20, wherein at least one of said bone engaging fasteners has said housing adjustably coupled to said screw.

22. The system of claim 21, wherein at least one of said guide members may be selectively manipulated to cause said adjustably coupled housing to rotate about said shaped end and thereby effect at least one of spinal compression and spinal distraction between said vertebral target sites.

23. The system of claim 20, wherein each of said first and second bone engaging fasteners has said housing adjustably coupled to said screw.

24. The system of claim 20, wherein said elongate connecting element spans between two vertebral target sites.

25. The system of claim 24, wherein said elongate connecting element spans at least three vertebral target sites.

26. The system of claim 25, including a third bone engaging fastener disposed between said first and second bone engaging fasteners.

27. The system of claim 20, wherein each of said shaped ends is at least partially spherical.

28. The system of claim 20, wherein at least one of said shaped ends is cannulated.

29. The system of claim 20, wherein said elongate connecting element is straight.

30. The system of claim 20, wherein said elongate connecting element is curved.

31. The system of claim 20, wherein each of said housings is equipped with a locking mechanism for locking said shaped ends of said connecting element within said respective housings.

32. The system of claim 31, wherein said locking mechanism comprises a threaded set screw for threaded engagement with threads formed within said respective housings.

33. The system of claim 20, wherein said guide members are configured such that they may be manipulated to introduce said bone engaging fasteners into said vertebral target sites.

34. The system of claim 20, wherein said lumen of each guide member is dimensioned to receive a sleeve member therethrough, said sleeve member comprising a distal end configured to releasably engage said housing.

35. The system of claim 34, wherein said sleeve member is configured to releasably engage said guide member.

36. The system of claim 20, wherein the elongate slot on each guide member has a length configured such that the enlarged opening is situated externally to the body entry site when said first and second guide members are mated with said first and second bone engaging fasteners and said first and second bone engaging fasteners are anchored to a spine.

* * * * *